US007589168B2

(12) United States Patent
Paris et al.

(10) Patent No.: US 7,589,168 B2
(45) Date of Patent: Sep. 15, 2009

(54) INHIBITION OF ANGIOGENESIS BY A-β PEPTIDES

(75) Inventors: Daniel Paris, Wesley Chapel, FL (US); Michael Mullan, Tampa, FL (US)

(73) Assignee: Roskamp Research LLC, Sarasota, FL (US)

( * ) Notice: Subject to any disclaimer, the term of this patent is extended or adjusted under 35 U.S.C. 154(b) by 0 days.

(21) Appl. No.: 10/217,584

(22) Filed: Aug. 12, 2002

(65) Prior Publication Data

US 2003/0077261 A1    Apr. 24, 2003

Related U.S. Application Data

(60) Provisional application No. 60/311,656, filed on Aug. 10, 2001.

(51) Int. Cl.
*A01N 43/42* (2006.01)
*A61K 31/44* (2006.01)
*A01N 37/18* (2006.01)
*A61K 38/00* (2006.01)

(52) U.S. Cl. .......................................... 530/300; 514/2

(58) Field of Classification Search ................... 514/44, 514/2–21; 536/23.1; 530/350, 174; 424/277.1
See application file for complete search history.

(56) References Cited

U.S. PATENT DOCUMENTS 5,981,471 A * 11/1999 Papathanassiu et al. ........ 514/2

FOREIGN PATENT DOCUMENTS

WO    WO 94/10569 A1    5/1994

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Thorne, et al. (2001) Clin. Pharmacokinet., 40(12): 907-46.*
Griffioen, et al. (2000) Pharmacological Reviews, 52(2): 237-68.*
Vagnucci, et al. (2003) Lancet, 361: 605-07.*
Sivakumar, et al. (2004) JAMA, 292(8): 972-77.*
Comments (2003) Lancet, 361 (9365) 1298-1300.*
Rudinger (1976) Peptide Hormones, University Park Press, Baltimore, MD., pp. 1-7.*
Bowie, et al. (1990) Science, 247 : 1306-10.*
Tarkowski et al. Increased intrathecal levels of the anglogenic factors VEGF and TGF-beta in Alzheimer's disease and vascular dementia. Neurobiology of Aging. 2002, vol. 23, pp. 237-243.
Paris et al. Soluble beta-amyloid peptides mediate vasoactivity via activation of a pro-inflammatory pathway. Neurobiology of Aging. 2000, vol. 21, pp. 183-197, especially p. 184, see entire document.
Mendis, D.B. et al. "SPARC/Osteonectin mRNA Is Induced in Blood Vessels Following Injury to the Adult Rat Cerebral Cortex" *Neurochemical Res.*, 1998, 23(8):1117-1123.

De Sauvage, F. et al. "A Novel mRNA of the A4 Amyloid Precursor Gene Coding for a Possibly Secreted Protein" *Science*, 1989, 245(4918):651-653.
Ellis, R.J. et al. "Cerebral amyloid angiopathy in the brains of patients with Alzheimer's disease: The CERAD experience, part XV" *Neurology*, 1996, 46:1592-1596.
Folkman, J. "How Is Blood Vessel Growth Regulated in Normal and Neoplastic Tissue?—G.H.A. Clowes Memorial Award Lecture" *Cancer Research*, Feb. 1986, 46:467-473.
Folkman, J. "What Is the Evidence That Tumors Are Angiogenesis Dependent?" *Journal of the National Cancer Institute*, Jan. 3, 1990, 82(1):4-6.
Hashimoto, T. et al. "Abnormal Balance in the Angiopoietin-Tie2 System in Human Brain Arteriovenous Malformations" *Circ. Res.*, 2001, 89:111-113.
Hashimura, T. et al. "Morphological Changes of Blood Vessels in the Brain with Alzheimer's Disease" *Jpn. J. Psychiatry Neurol.*, 1991, 45(3):661-665.
Johnson, K. and M.S. Albert "Perfusion abnormalities in prodromal AD" *Neurobiology of Aging*, 2000, 21:289-292.
Kalaria, R.N. "The Blood-Brain Barrier and Cerebrovascular Pathology in Alzheimer's Disease" *Ann. N.Y. Acad. Sci.*, 1999, 893:113-125.
Kimura, T. et al. "Observations of Microvessels in the Brain with Alzheimer's Disease by the Scanning Electron Microscopy" *Jpn. J. Psychiatry Neurol.*, 1991, 45(3):671-676.
Kruger, E.A. et al. "Endostatin Inhibits Microvessel Formation in the ex Vivo Rat Aortic Ring Angiogenesis Assay" *Biochem. Biophys. Res. Commun.*, 2000, 268:183-191.
Nagata, K. et al. "Vascular and metabolic reserve in Alzheimer's disease" *Neurobiology of Aging*, 2000, 21:301-307.
Naidu, A. et al., "β-Amyloid Peptide Produced in Vitro Is Degraded by Proteinases Released by Cultured Cells" *J. Biol. Chem.*, 1995, 270(3):1369-1374.
Nicosia, R.F. et al. "Large-vessel endothelium switches to a microvascular phenotype during angiogenesis in collagen gel culture of rat aorta" *Atherosclerosis*, 1992, 95:191-199.
Nicosia, R.F. et al. "Endogenous Regulation of Angiogenesis in the Rat Aorta Model" *Amer. J. Path.*, Nov. 1997, 151(5):1379-1386.

(Continued)

*Primary Examiner*—Robert M Kelly
(74) *Attorney, Agent, or Firm*—Margaret B. Brivanlou; Richard M. Enmon, Jr.; King & Spalding LLP

(57) ABSTRACT

The present invention provides methods and compositions for treating diseases and pathological conditions or processes mediated by undesired and/or uncontrolled angiogenesis (characterized as "angiogenic diseases"), in particular cancer, by increasing the in vivo concentration of the Aβ peptide, within a patient suffering from such diseases, conditions or processes. The present invention also concerns diagnostic methods and kits for the detection and measurement of antiangiogenic Aβ peptide activity in biological fluids and tissues. Such diagnostic methods and kits can be utilized to screen compounds for potential therapeutic activity in the treatment of angiogenic diseases such as Alzheimer's disease and cancer.

8 Claims, 19 Drawing Sheets

OTHER PUBLICATIONS

Ponte, P. et al. "A new A4 amyloid mRNA contains a domain homologous to serine proteinase inhibitors" *Nature*, Feb. 1988, 331:525-527.

Sisodia, S. et al. "Role of the β-amyloid protein in Alzheimer's disease" *FASEB. J.*, 1995, 9:366-370.

Slevin, M. et al., "Serial Measurement of Vascular Endothelial Growth Factor and Transforming Growth Factor-β1 in Serum of Patients With Acute Ischemic Stroke" *Stroke*, 2000, 31:1863-1870.

Weidner, N. et al. "Tumor Angiogenesis and Metastasis—Correlation in Invasive Breast Carcinoma" *The New England Journal of Medicine*, 1991, 324(1):1-8.

Yoshikai, S. et al. "Genomic organization of the human amyloid beta-protein precursor gene" *Gene*, 1990, 87:257-263.

Paris D. et al. Inhibition of Angiogenesis by Aβ Peptides, Angiogenesis, 2004; 7:75-85.

Ho L. et al. The Alternatively Spliced Kunitz Protease Inhibitor Domain Alters Amyloid β Proteins Precursor Processing and Amyloid β Protein Production in Cultured Cells, J. Biol. Chem., 1996; 271(48):30929-30394.

Ramakrishnan et al., 2001, Targeting tumor vasculature using VEGF-toxin Conjugates. Methods Mol Biol 166:219-234.

* cited by examiner

Control

Aβ 1μM

Aβ 5μM

FIG. 2A  FIG. 2B  FIG. 2C
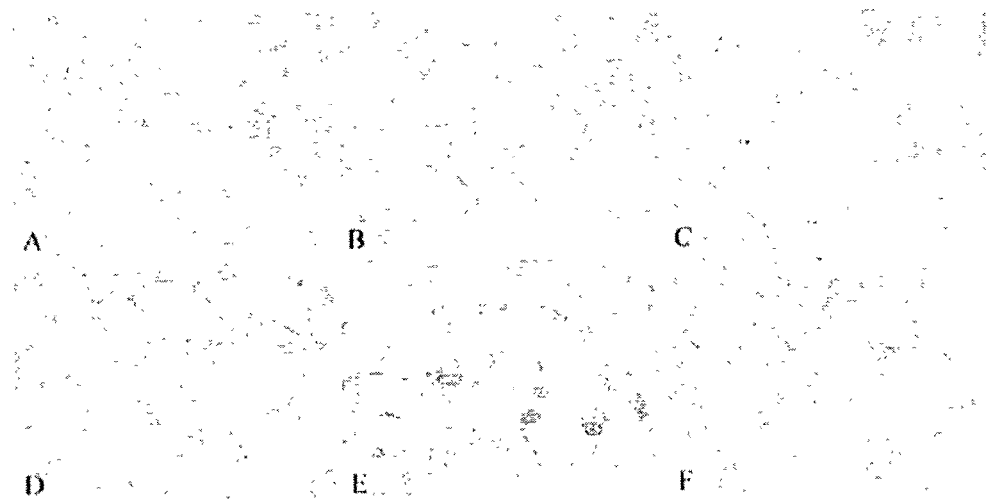
FIG. 2D  FIG. 2E  FIG. 2F
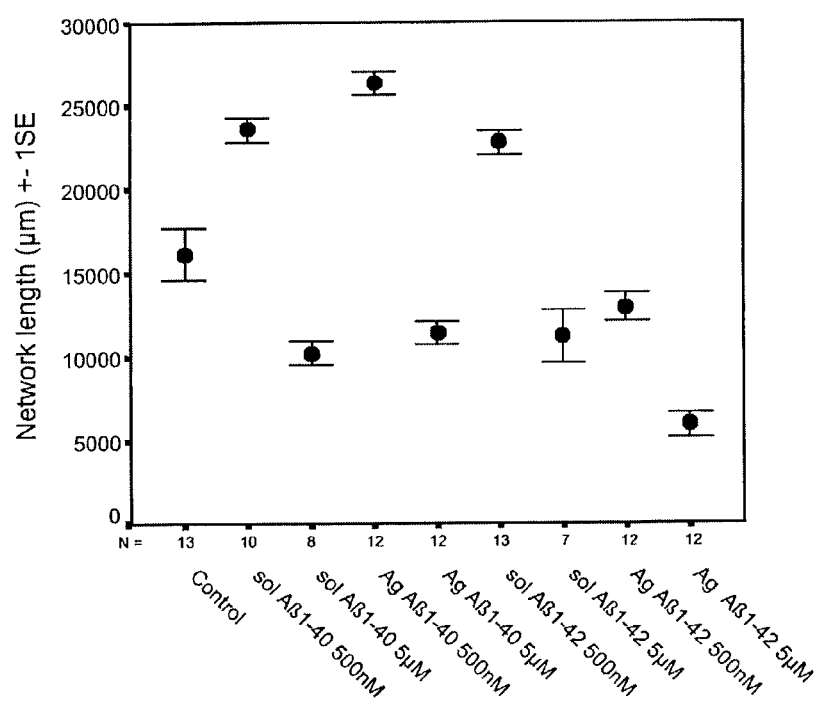
FIG. 2G

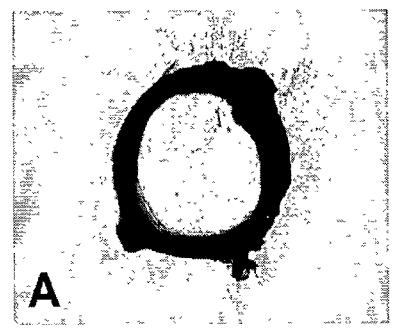 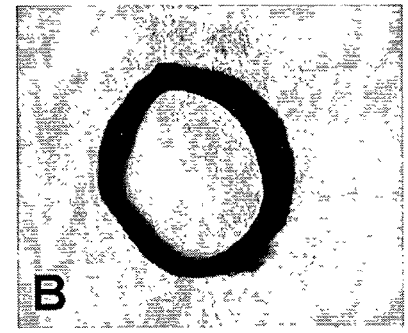
FIG. 3A  FIG. 3B
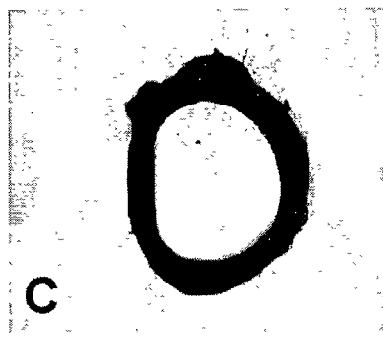 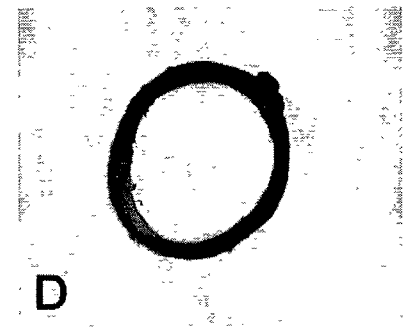
FIG. 3C  FIG. 3D
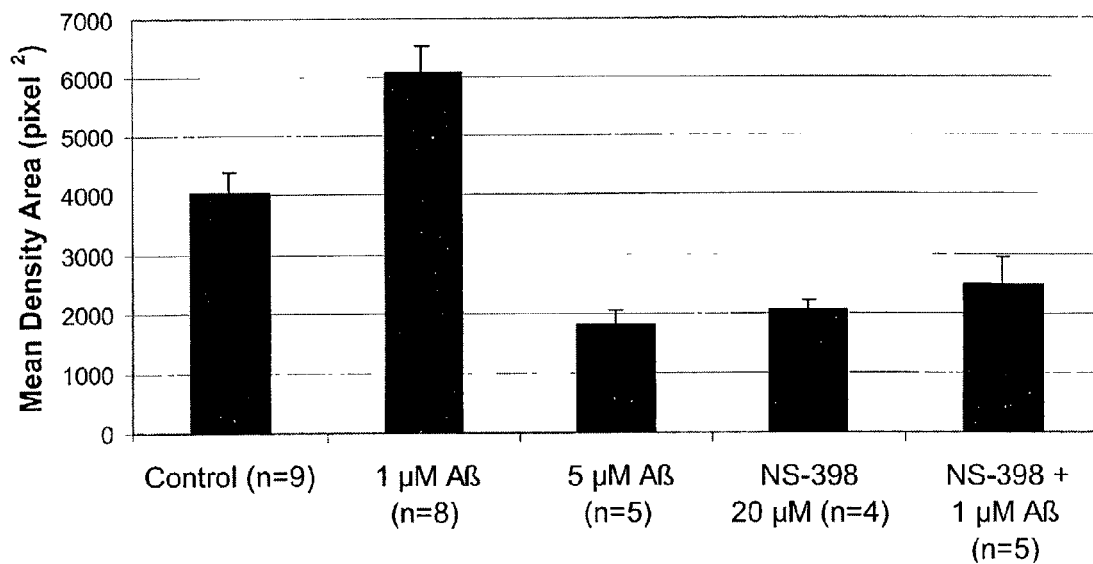
FIG. 4

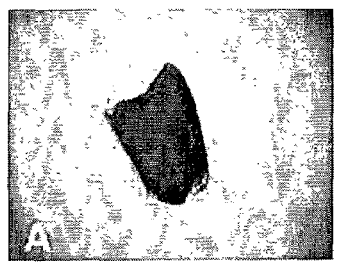 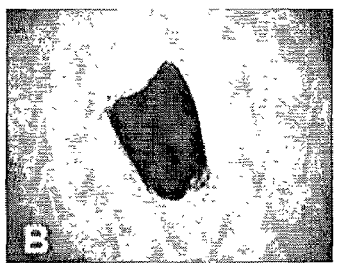 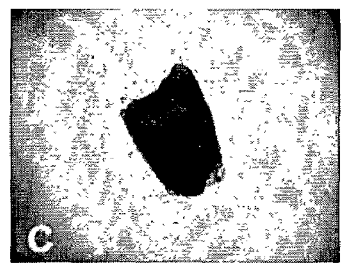
FIG. 5A  FIG. 5B  FIG. 5C
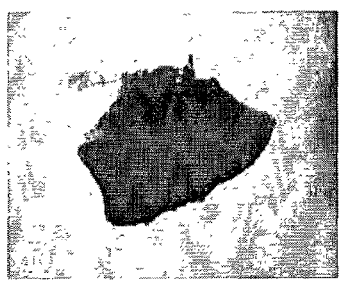 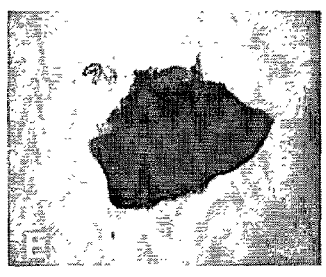 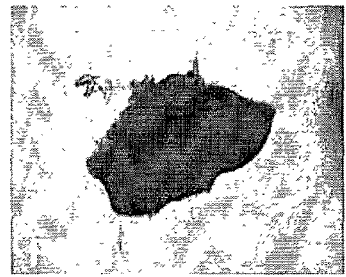
FIG. 5D  FIG. 5E  FIG. 5F
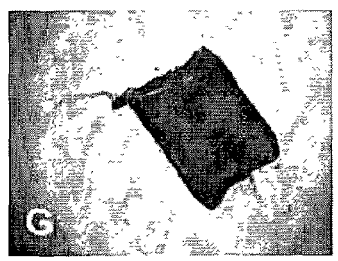 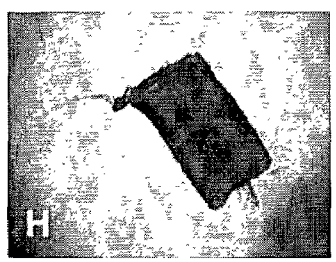 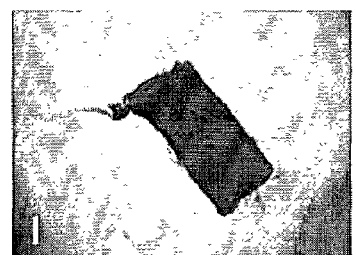
FIG. 5G  FIG. 5H  FIG. 5I
Day 6  Day 7  Day 9

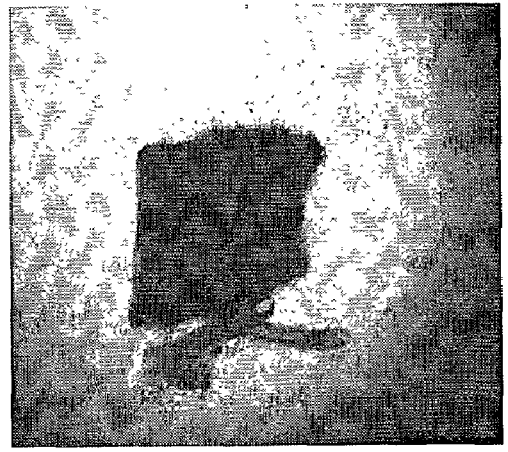
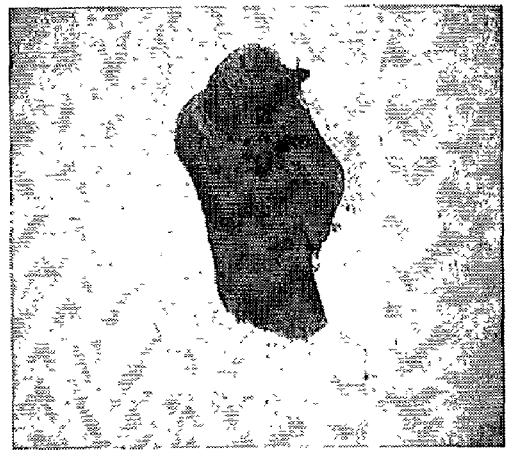
FIG. 7A          FIG. 7B
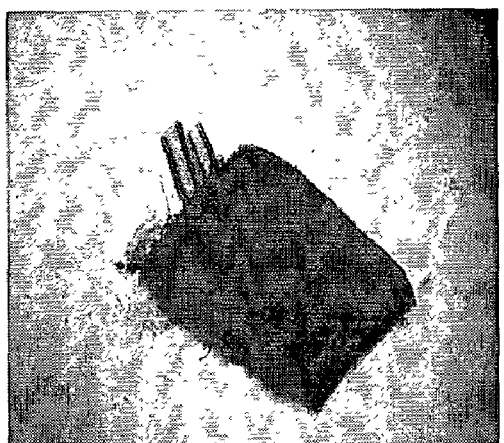
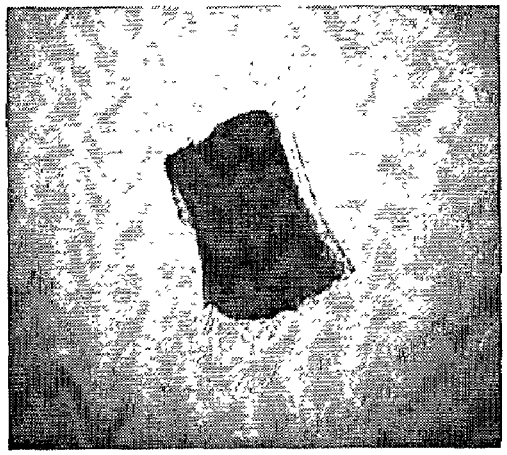
FIG. 7C          FIG. 7D
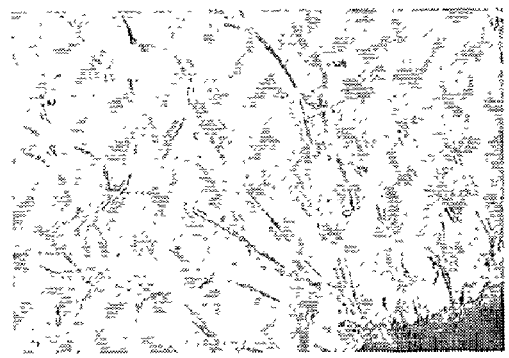
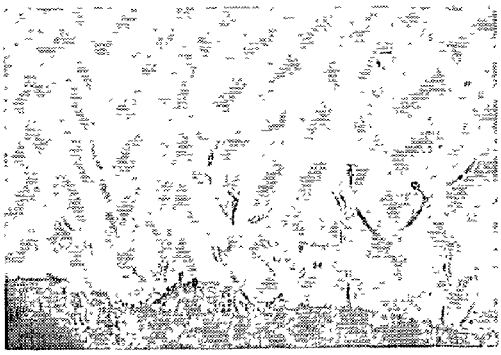
FIG. 7E          FIG. 7F FIG. 17A
FIG. 17B
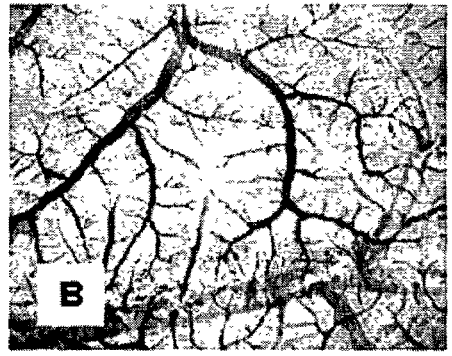
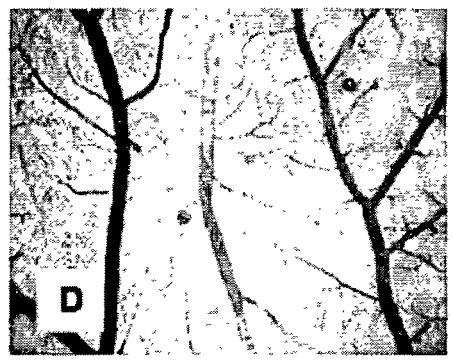
FIG. 17C
FIG. 17D
| Peptide Dose/CAM | CAM showing an antiangiogenic response | |
|---|---|---|
| | Scrambled Aβ | Aβ1-40 |
| 1 μg | 0% (12) | 0% (13) |
| 10 μg | 0% (11) | 0% (13) |
| 50 μg | 0% (8) | 22% (23) |
| 100 μg to 250 μg | 0% (18) | 38% (13) |
FIG. 17E FIG. 18A
FIG. 18B
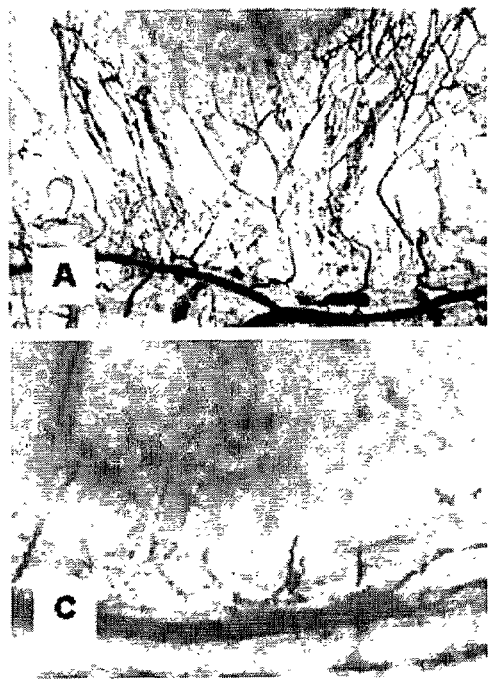
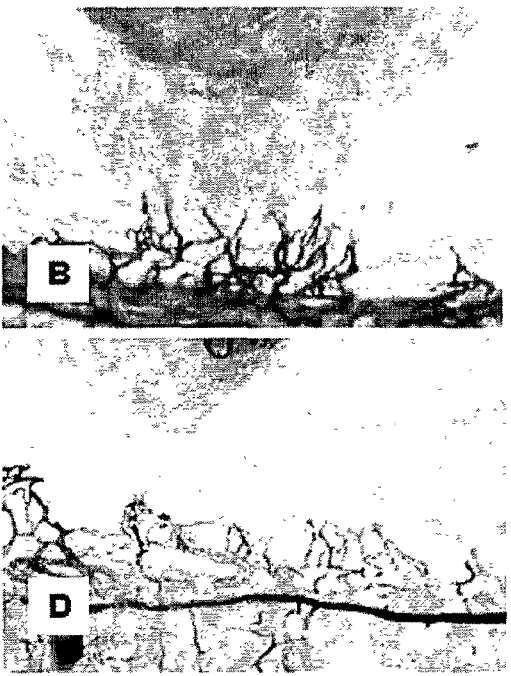
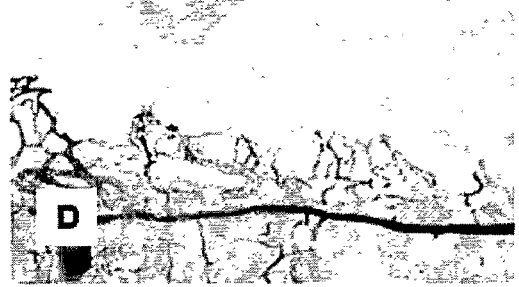
FIG. 18C
FIG. 18D
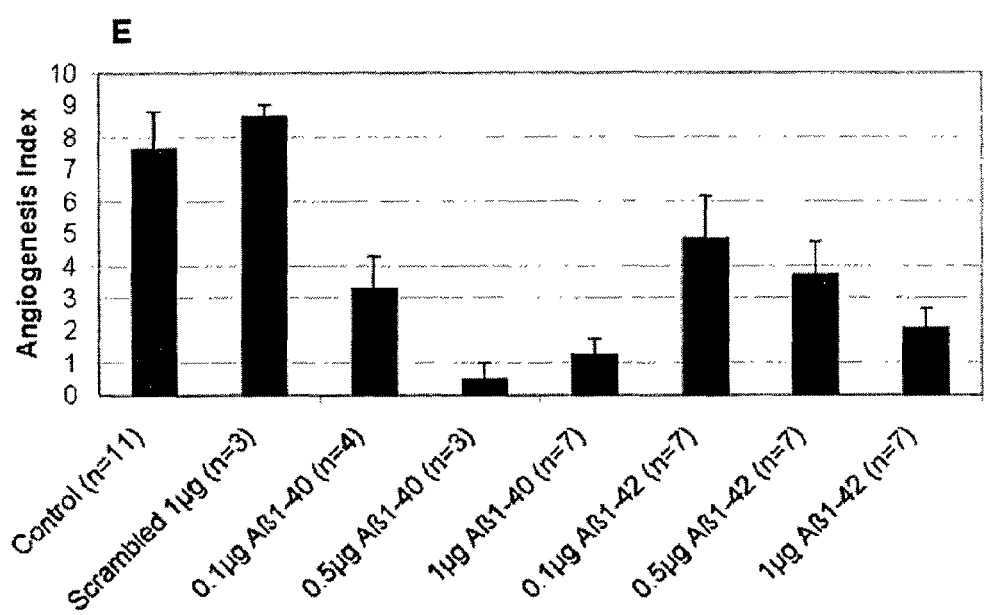
FIG. 18E

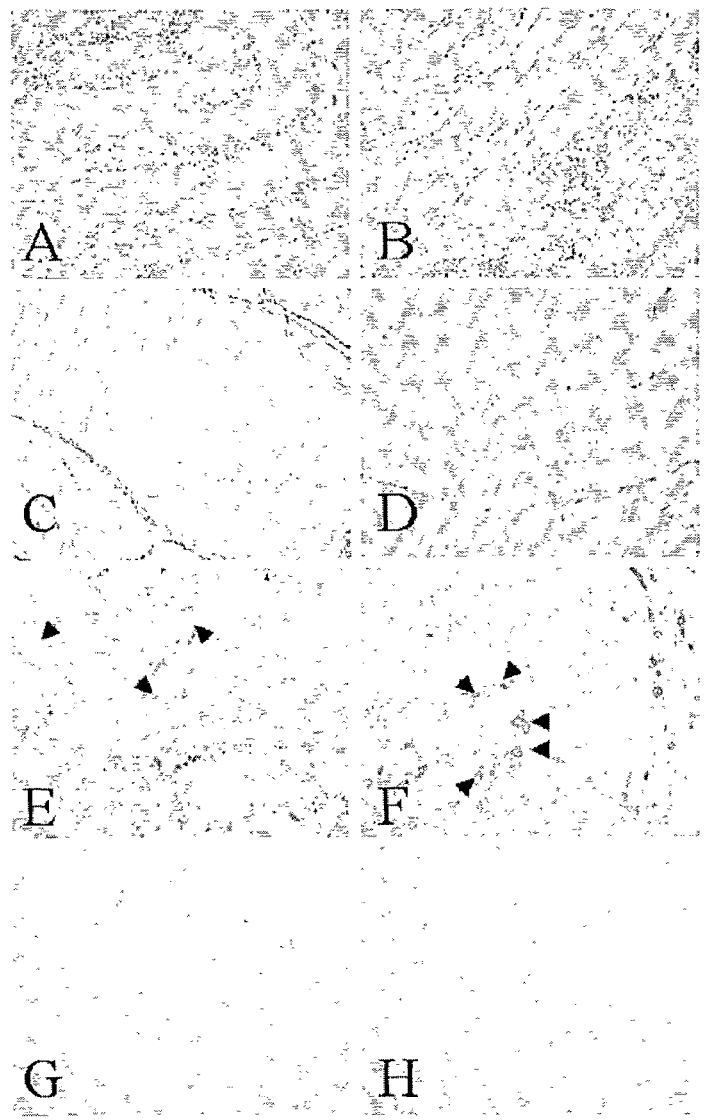
FIG. 19A FIG. 19B
FIG. 19C FIG. 19D
FIG. 19E FIG. 19F
FIG. 19G FIG. 19H
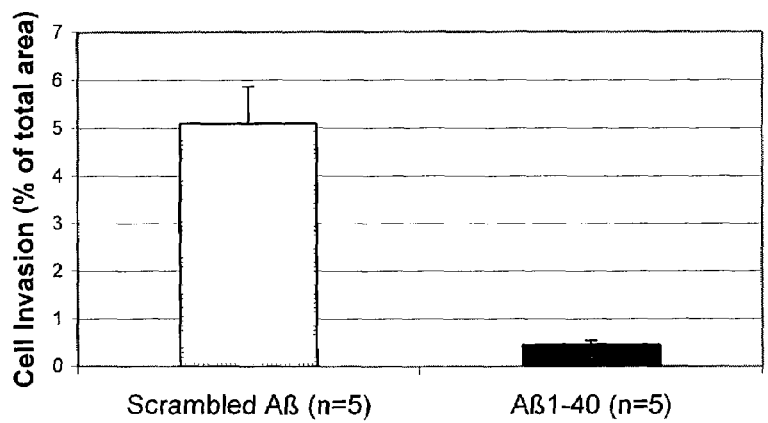
FIG. 19I

INHIBITION OF ANGIOGENESIS BY A-β PEPTIDES

CROSS-REFERENCE TO RELATED APPLICATION

This application claims the benefit of provisional patent application Ser. No. 60/311,656, filed Aug. 10, 2001, which is hereby incorporated by reference in its entirety, including all nucleic acid sequences, amino acid sequences, figures, tables, and drawings.

BACKGROUND OF THE INVENTION

Alzheimer's disease (AD) is the major cause of dementia in the elderly in Western countries, and is characterized by the progressive accumulation of intracellular neurofibrillary tangles, extracellular parenchymal senile plaques, and cerebrovascular deposits (Sissodia et al. *FASEB. J.* 9:366-370 (1995)). The principal component of senile plaques and cerebrovascular deposits is the β-amyloid peptide, the aggregated form of which consists of the 39-43 amino acid residue Aβ peptides that are proteolytically derived from the amyloid precursor protein (APP) (Naidu et al. *J. Biol. Chem.* 270: 1369-1374 (1995)). Vascular pathology is the norm in advanced cases of AD, with cerebral amyloid angiopathy (CAA) being one of the most common abnormalities detected at autopsy (Ellis et al. *Neurology* 46:1592-1596 (1996)). Certain vascular lesions, such as microvascular degeneration affecting the cerebral endothelium and periventricular white matter lesions, are evident in most AD cases (Ellis et al. *Neurology* 46:1592-1596 (1996); Kalaria, *Ann. N.Y. Acad. Sci.* 893:113-125 (1999)). Furthermore, morphological alterations have been observed in AD brain microvessels and capillaries; in particular, terminal arterioles frequently have focal constriction and smooth muscle cells with an irregular shape and arrangement (Hashimura et al. *Jpn. J. Psychiatry Neurol.* 45:661-665 (1991)). Capillaries in AD brain typically show an abnormal abluminal surface with irregular constriction and dilatation along their paths (Kimura et al. *Jpn. J. Psychiatry Neurol.* 45:671-676 (1991)). Functional imaging techniques including positron emission tomography (PET) and single photon emission computerized tomography (SPECT) have revealed the existence of hypoperfusion in individuals prior to the time that they meet clinical criteria for AD suggesting that vascular abnormalities occur early during the disease process (Nagata et al. *Neurobiology of Aging* 21:301-307 (2000); Johnson et al. *Neurobiology of Aging* 21:289-292 (2000)). In other disorders involving cerebrovascular damage (such as traumatic brain injury, stroke and brain arteriovenous malformation), angiogenesis is a prominent response (Mendis et al. *Neurochem. Res.* 23:1117-23 (1998); Slevin et al. *Stroke* 31:1863-70 (2000); Hashimoto et al. *Circ. Res.* 89:111-3 (2001)). Given the plethora of reports on cerebrovascular damage in AD brain, the induction of an angiogenic reparative response would be expected, although there has been very little work in this area.

Several assays have been developed to study the specific steps involved in the angiogenic process (adhesion, migration, growth, invasion and differentiation). Knowledge of the effects of Aβ on angiogenesis would be of value in understanding its role in the micro-cerebrovascular abnormalities observed in AD.

BRIEF SUMMARY OF THE INVENTION

The present invention provides methods and compositions for treating pathological conditions mediated by undesired and/or uncontrolled angiogenesis (characterized as "angiogenic diseases".) by increasing the in vivo concentration of the Aβ peptide, or biologically active fragments or variants of the Aβ peptide, within a patient suffering from such diseases, conditions, or processes. In specific embodiments, the methods of the subject invention involve increasing the in vivo concentration of one or more of the following Aβ peptides within a patient: the full length $A\beta_{1-43}$ peptide, the $A\beta_{1-42}$ peptide, and the $A\beta_{1-40}$ peptide, or biologically active fragments or variants thereof, such as mutants of the $A\beta_{1-42}$ peptide.

The present invention also concerns diagnostic methods and kits for detection and measurement of anti-angiogenic Aβ peptide activity in biological fluids and tissues.

The subject invention also pertains to diagnostic methods and kits to screen for compounds that are potentially therapeutic in treatment of Alzheimer's disease by interfering with the anti-angiogenic effect of the Aβ peptide.

BRIEF DESCRIPTION OF THE DRAWINGS

FIG. 1D shows the quantitative determination of endothelial cell migration. The number in parenthesis represents the number of field analyzed. Analysis of Variance (ANOVA) revealed significant main effects of Aβ dose ($P<0.001$). Post-hoc testing showed significant differences between control and 1 μM $A\beta_{1-40}$ ($P<0.03$), between control and 5 μM $A\beta_{1-40}$ ($P<0.004$) and between 1 μM $A\beta_{1-40}$ and 5 μM $A\beta_{1-40}$ ($P<0.001$).

FIGS. 2A-2G show modulation of capillary network formation by soluble and aggregated forms of $A\beta_{1-40}$ and $A\beta_{1-42}$ in MATRIGEL reconstituted basement membrane. Human brain endothelial cells were grown without $A\beta_{1-40}$ (FIG. 2A), with 500 nM freshly solubilized $A\beta_{1-40}$ (FIG. 2B), with 5 μM freshly solubilized $A\beta_{1-40}$ (FIG. 2C), with 500 nM freshly solubilized $A\beta_{1-42}$ (FIG. 2D), with 5 μM freshly solubilized $A\beta_{1-42}$ (FIG. 2E), with 500 nM aggregated $A\beta_{1-42}$ (FIG. 2F). Quantification of network length by Image analysis (FIG. 2G), the numbers on the x axis represent the number of 4× fields analyzed. ANOVA revealed significant main effects of Aβ dose ($P<0.001$) as well as significant difference between groups ($P<0.001$). Post-hoc testing showed significant difference between control and 500 nM (sol $A\beta_{1-40}$) freshly solubilized $A\beta_{1-40}$ ($P<0.001$), control and 5 μM sol $A\beta_{1-40}$ ($P<0.005$), control and 500 nM aggregated (Ag) $A\beta_{1-40}$ ($P<0.001$), control and 5 μM Ag $A\beta_{1-40}$ ($P<0.02$), control and 500 nM sol $A\beta_{1-42}$ ($P<0.001$), control and 5 μM sol $A\beta_{1-42}$ ($P<0.05$), control and 5 μM Ag $A\beta_{1-42}$ ($P<0.001$) but no significant difference between control and 500 nM Ag $A\beta_{1-42}$ ($P=0.28$). Post-hoc testing also reveals significant differences between 5 μM Ag $A\beta_{1-40}$ and 5 μM Ag $A\beta_{1-42}$ ($P<0.003$).

FIGS. 3A-3D show the effect of $A\beta_{1-40}$ and NS-398 on microvessel outgrowths in rat aortic rings; (FIG. 3A) Control medium, (FIG. 3B) 1 μM $A\beta_{1-40}$, (FIG. 3C) 5 μM $A\beta_{1-40}$, and (FIG. 4D) 20 μM NS-398. Rat aortic rings were photographed on Day 5.

FIG. 4 shows the quantification of microvessel outgrowths with $A\beta_{1-40}$ and NS-398 treatment on rat aortic rings. Image analysis of rat aortic rings demonstrates that at 1 µM, $A\beta_{1-40}$ stimulates the angiogenic process whereas at 5 µM $A\beta_{1-40}$ displays potent anti-angiogenic activity. NS-398, a selective cyclooxygenase-2 (COX-2) inhibitor displays anti-angiogenic activity and is able to oppose the pro-angiogenic effect of 1 µM $A\beta_{1-40}$. Error bars represent standard error and the number in brackets represents the number of aortic rings analyzed. ANOVA revealed significant main effects of $A\beta$ dose (P<0.001) and NS-398(P<0.001). Post-hoc testing showed significant differences between control and 1 µM $A\beta_{1-40}$ (P<0.005), control and 5 µM $A\beta_{1-40}$ (P<0.03), control and NS-398 (P<0.03), but not between NS-398 and NS-398+1 µM $A\beta_{1-40}$ (P=0.674).

FIGS. 5A-5I show the anti-angiogenic activity of $A\beta_{1-40}$ on cow middle cerebral artery rings. The formation of microvessel outgrowths was followed at Day 6, Day 7 and Day 9. FIGS. 5A, 5B, and 5C show cerebral artery rings in control medium; FIGS. 5D, 5E, and 5F show cerebral artery rings with 1 µM $A\beta_{1-40}$; and FIGS. 5G, 5H, and 5I show cerebral artery rings with 5 µM $A\beta_{1-40}$.

FIGS. 7A-7F show the anti-angiogenic effect of $A\beta_{1-40}$ and NS-398 on human middle cerebral artery rings. FIG. 7A shows cerebral artery rings in control medium. FIG. 7B shows cerebral artery rings with 1 µM $A\beta_{1-40}$. FIG. 7C shows cerebral artery rings with 5 µM $A\beta_{1-40}$. FIG. 7D shows cerebral artery rings with 20 µM NS-398. Human middle cerebral artery rings were photographed on Day 9 using a 2× objective. FIGS. 7E and 7F show the tube-like structures (original magnification 100×) attached to the artery wall of human cerebral middle artery rings, respectively, in control medium and after treatment with 5 µM of $A\beta_{1-40}$ for 9 days.

FIG. 9A shows artery rings in control medium. FIG. 9B shows artery rings with 1 µM scramble $A\beta_{1-40}$. FIG. 9C shows artery rings with 5 µM scramble $A\beta_{1-40}$ (human middle cerebral artery rings were photographed on day 9). FIG. 9D shows quantification by image analysis of microvessel outgrowths, which demonstrates that the angiogenesis process is not altered by 1 µM or 5 µM of scramble $A\beta_{1-40}$.

(FIG. 10C) Smooth muscle cells isolated from the rat brain microvasculature were used as a positive control for α-smooth muscle actin and as a negative control for factor VIII immunostaining. FIGS. 10D, 10E and 10F depict the corresponding phase contrast observation for FIGS. 10A, 10B and 10C, respectively (original magnification 100×.

FIG. 11A shows control and FIG. 11C shows Tg APPsw mice aortic rings at day 5. FIG. 11B shows control and FIG. 11D shows Tg APPsw mice aortic rings at day 6. FIG. 11E and FIG. 11F show microvessel outgrowths (original magnification 100×) attached to the artery wall of aortic rings from control and Tg APPsw mice respectively.

FIG. 13E shows a histogram depicting the vascular densities in the cortex and the hippocampus of control and Tg APPsw mice (n=3 in each group). ANOVA revealed significant main effects for transgenicity on capillary density (P<0.001) and for the area of the brain examined (P<0.001). Post-hoc comparisons showed significant differences between the cortex and hippocampus (P<0.001) for both control and Tg APPsw mice, between control cortex and Tg APPsw cortex (P<0.001) and between control hippocampus and Tg APPsw hippocampus (P<0.001).

FIGS. 15B-15G show representative pictures depicting the vascularization of A-549 tumors detected by labeling endothelial cells with CD31 [(FIG. 15B) control tumor, (FIG. 15C) scrambled Aβ treated tumor, and (FIG. 15D) Aβ$_{1-40}$ treated tumor and with factor VIII [(FIG. 15E) control tumor (FIG. 15F) scrambled Aβ treated tumor and (FIG. 15G) Aβ$_{1-40}$ treated tumor]. FIG. 15H is a histogram showing the mean microvessel count per tumor. ANOVA revealed significant main effect for Aβ$_{1-40}$ treatment (P<0.001) but no significant main effect for scrambled Aβ treatment (P=0.314). Post-hoc analysis showed significant differences between control tumors and Aβ$_{1-40}$ treated tumors (P<0.002) but no significant difference between control tumors and tumors treated with scrambled Aβ (P=0.941).

FIGS. 16B and 16C are representative pictures depicting the vascularization of U87-MG tumors detected by labeling endothelial cells with CD31: (FIG. 16B) control tumor and (FIG. 16C) Aβ$_{1-40}$ treated tumor. FIG. 16D is a histogram, showing the mean microvessel count per tumor. t-test for independent sample revealed significant difference (P<0.05) between microvessel count in control and Aβ treated tumors.

FIGS. 17A-17H show the effect of Aβ$_{1-40}$ and scrambled Aβ peptides in the chick chorionic allantoid membrane (CAM) model of angiogenesis. Methylcellulose disks impregnated with different doses of Aβ$_{1-40}$ or scrambled Aβ (ranging from 1 µg to 250 µg) were applied on 6-day-old CAMs. After 48 hours of incubation, CAMs were perfused with colloidal carbon, fixed and photographed. Representative pictures of CAMs of chick embryo incubated for 48 hours with a methylcellullose disk impregnated with vehicle alone (distilled water) (FIG. 17A), with 1 µg of Aβ$_{1-40}$ (FIG. 17B), with 50 µg of scrambled Aβ (FIG. 17C) and with 50 µg of Aβ$_{1-40}$ (FIG. 17D). As shown in FIG. 17E, no difference in vascular response was discernible between control conditions (n=7), and scrambled Aβ for the dose range used (1 microgram to 250 micrograms), 1 µg (n=13) or 10 µg of Ab1-40 (n=13). 22% of the CAMs treated with 50 µg of Ab1-40 (n=23) and 38% of the CAMs treated with Aβ$_{1-40}$ doses ranging from 150 µg to 250 µg (n=13) showed inhibition of angiogenesis.

FIGS. 18A-18E show the effect of Aβ$_{1-40}$, Aβ$_{1-42}$ and scrambled Aβ in the rat corneal model of angiogenesis. Representative flat-mount photomicrographs of rat corneas (original magnification ×100) 7 days after implantation of hydron pellets. FIG. 18A shows bFGF alone; FIG. 18B shows bFGF and 0.1 µg Aβ$_{1-40}$; FIG. 18C shows bFGF and 0.5 µg Aβ$_{1-40}$; and FIG. 18D shows bFGF and 1 µg Aβ$_{1-40}$. FIG. 18E shows summary data of the in vivo angiogenic response to bFGF, and bFGF plus Aβ$_{1-40}$, Aβ$_{1-42}$ and scrambled Aβ in the rat corneal assay. Angiogenesis indexes are expressed as mean±SE. ANOVA revealed significant main effects of Aβ$_{1-40}$ dose (P<0.001) and Aβ$_{1-42}$ dose (P<0.003) but no significant main effect of scrambled Aβ (P=0.577). Post-hoc analysis showed significant differences between control and 1 mg of Aβ$_{1-40}$ (P<0.001), between control and 0.5 mg of Ab1-40 (P<0.01), between control and 1 µg of Aβ$_{1-42}$ (P<0.007), between control and 0.5 mg of Aβ$_{1-42}$ (P<0.05) but no significant difference between control and scrambled Aβ (P=0.997).

FIGS. 19A-19I show the effect of Aβ$_{1-40}$ and scrambled Aβ on bFGF-induced angiogenesis in MATRIGEL plugs in vivo. Representative assay showing Hematoxylin staining of MATRIGEL plug sections from mice treated with scrambled Aβ (FIGS. 19A and 19B) or with Aβ$_{1-40}$ (FIGS. 19C and 19D). PECAM-1 immunostaining (brown staining) revealing the presence of endothelial cells forming vessels (arrows) in sections of MATRIGEL plugs isolated from the scrambled Aβ treated group (FIGS. 19E and 19F) and the absence of vessel formation in the MATRIGEL plugs isolated from Aβ$_{1-40}$ treated animals (FIGS. 19G and 19H). FIG. 19I shows a histogram representing the amount of total cellular invasion in MATRIGEL plugs isolated from animals (5 mice for each treatment group) treated with scrambled Aβ (50 mg/kg/day) and with Aβ$_{1-40}$ (50 mg/kg/day). t-test for independent samples revealed a significant difference between the Aβ and scrambled Aβ treatment groups (P<0.001).

FIG. 20A shows inhibition of capillary network formation (of human brain endothelial cells) by soluble forms of the Dutch Aβ$_{1-40}$ peptide in MATRIGEL reconstituted basement membrane. Human brain endothelial cells were grown without Dutch Aβ$_{1-40}$ peptide (control) or with various doses of the Dutch Aβ$_{1-40}$ peptide (500 nM to 10 µM). In the quantification of network length by Image analysis, the numbers on the x-axis represent the number of 4× fields analyzed, as shown in FIG. 20B. ANOVA revealed significant main effect of Dutch Aβ$_{1-40}$ peptide (P<0.001) showing that soluble Dutch Aβ$_{1-40}$ peptide is anti-angiogenic. FIG. 20C shows a comparison of the effects of the soluble Dutch Aβ$_{1-40}$, soluble wild type Aβ$_{1-40}$ and soluble wild type Aβ$_{1-42}$ peptides in the capillary network assay. ANOVA showed significant main effects for soluble Dutch Aβ$_{1-40}$, soluble wild type Aβ$_{1-40}$ and soluble wild type Aβ$_{1-42}$ peptides (P<0.01). Post-hoc testing revealed significant difference between control and the different peptides used (P<0.04) but no significant differences (P>0.05) between 5 µM of soluble Aβ$_{1-40}$ and 500 nM of soluble Dutch Aβ$_{1-40}$ or between 5 µM of soluble Aβ$_{1-42}$ and 500 nM of soluble Dutch Aβ$_{1-40}$ showing that the Dutch Aβ$_{1-40}$ peptide is 10 time more potently anti-angiogenic than soluble Aβ$_{1-40}$ or soluble Aβ$_{1-42}$.

BRIEF DESCRIPTION OF THE SEQUENCES

Figure 1A:
FIGS. 1A-1D show modulation of endothelial cell migration by Aβ. Human brain endothelial cells were resuspended in EBM with 4% FBS at density $4\times10_4$ cells/ml. Cells (0.5 ml) were placed in the upper chamber and migration was initiated by placing 1 ml of the same media containing 0 μM (FIG. 1A), 1 μM (FIG. 1B), or 5 μM (FIG. 1C) of freshly solubilized $A\beta_{1-40}$ in the bottom chamber. After 20 hours, the cells on the upper side of the membrane were removed by cotton swab and the membrane was cut out, fixed, stained and cells migrated were numerated.
Figure 1B:
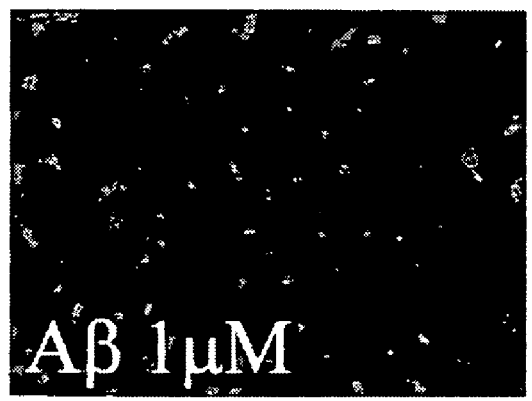
Figure 1C:
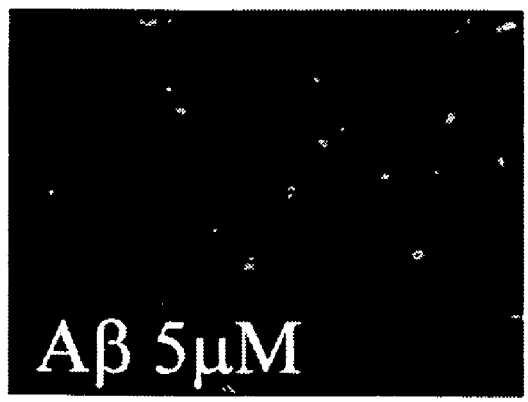
Figure 1A:
Figure 1B:
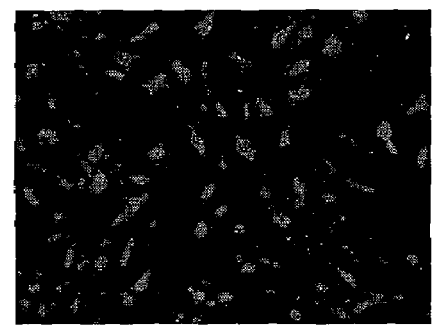
Figure 1C:
Figure 1D:
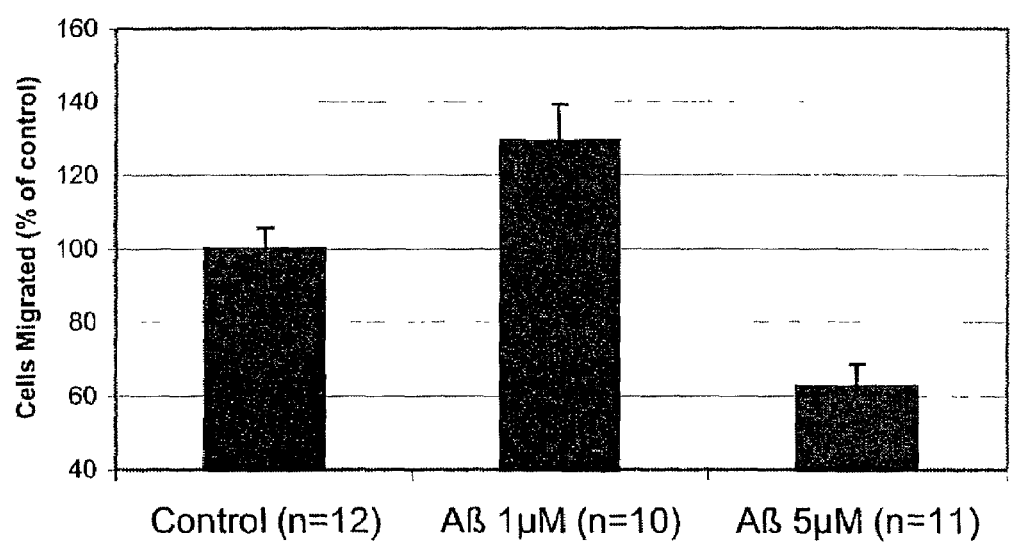
Figure 6:
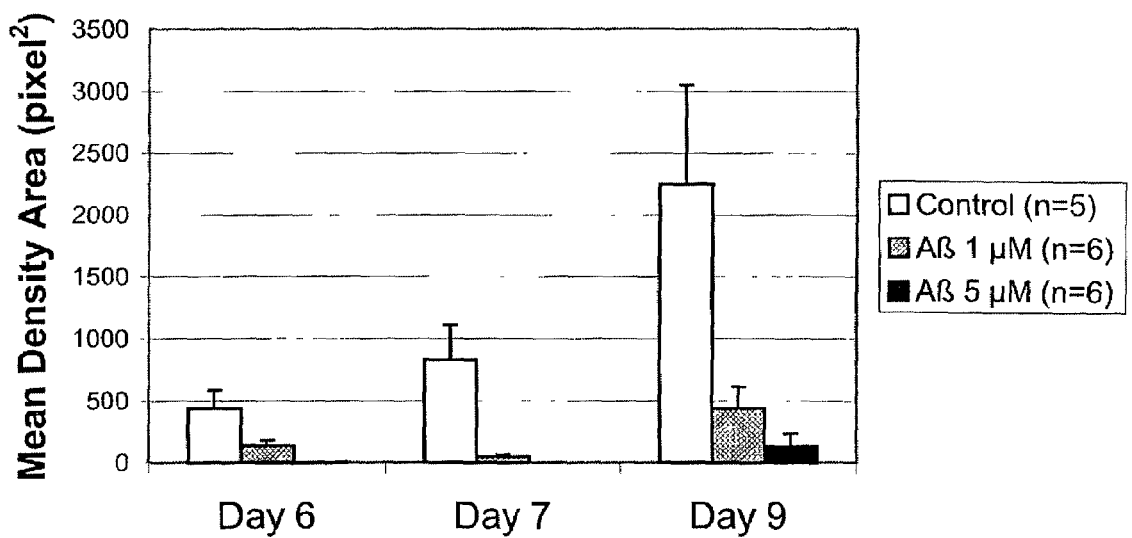
FIG. 6 shows the quantification of microvessel outgrowths in response to $A\beta_{1-40}$ treatment on cow middle cerebral artery rings. Image analysis of cow middle cerebral artery rings demonstrates the anti-angiogenic activity of $A\beta_{1-40}$. ANOVA revealed significant main effects of $A\beta$ dose (P<0.001) and time (P<0.05), and an interactive term between them (P=0.035). Post-hoc testing across day 6 to day 9 showed significant difference between control and 1 µM $A\beta_{1-40}$ (P<0.001) and between control and 5 µM $A\beta_{1-40}$ (P<0.001), but no significant difference between 1 µM $A\beta_{1-40}$ and 5 µM $A\beta_{1-40}$ (P=0.707).

SEQ ID NO. 1 is the amino acid sequence of the human Aβ$_{1-43}$ peptide.

SEQ ID NO. 2 is the amino acid sequence of the human Aβ$_{1-42}$ peptide.

SEQ ID NO. 3 is the amino acid sequence of the human Aβ$_{1-40}$ peptide.

SEQ ID NO. 4 is the amino acid sequence of the scrambled Aβ$_{1-40}$ peptide.

SEQ ID NO. 5 is the amino acid sequence of the human amyloid precursor protein (APP).

SEQ ID NO. 6 is the nucleotide sequence encoding the human APP (Miller et al. *Nature* 331(6156), 525-527, 1988;

de Sauvage et al. *Science* 245(4918), 651-653, 1989; Yoshikai et al. *Gene* 87(2), 257-263, 1990).

SEQ ID NO. 7 is the 21G-Aβ$_{1-42}$ (Flemish) mutant peptide.
SEQ ID NO. 8 is the 22Q-Aβ$_{1-42}$ (Dutch) mutant peptide.
SEQ ID NO. 9 is the 22K-Aβ$_{1-42}$ (Italian) mutant peptide.
SEQ ID NO. 10 is the 22G-Aβ$_{1-42}$ (Arctic) mutant peptide.
SEQ ID NO. 11 is the 23N-Aβ$_{1-42}$ (Iowa) mutant peptide.

DETAILED DISCLOSURE OF THE INVENTION

The subject invention concerns a method of modulating angiogenesis within a patient by modulating the amount of anti-angiogenic Aβ peptide activity within the patient. In one aspect, the subject invention concerns a method of inhibiting angiogenesis within a patient in need of anti-angiogenesis therapy by increasing the in vivo concentration of Aβ peptide, or biologically active fragments or variants thereof, within the patient.

In specific embodiments, the methods of the subject invention involve increasing the in vivo concentration of one or more of the following Aβ peptides within a patient: the full length Aβ$_{1-43}$ peptide, the Aβ$_{1-42}$ peptide, and the Aβ$_{1-40}$ peptide, or biologically active fragments or variants thereof.

The subject invention also includes methods of treating angiogenesis-mediated diseases in a patient by increasing the in vivo concentration of Aβ peptide, or a biologically active fragment or variant thereof, to an amount effective to inhibit angiogenesis within the patient. The in vivo concentration of Aβ peptide, or a biologically active fragment or variant thereof, can be increased, for example, by exogenous administration of the Aβ peptide, or a biologically active fragment or variant thereof. The in vivo concentration of Aβ peptide, or a biologically active fragment or variant thereof, can also be increased by increasing or up-regulating the functional expression of the Aβ peptide, or a biologically active fragment or variant thereof.

In one embodiment, the subject invention provides a treatment for a pathological condition selected from the group consisting of cancer, arthritis, atherosclerosis, psoriasis, macular degeneration, and diabetic retinopathy by administering to the patient a therapeutically effective amount of an Aβ peptide, or a biologically active fragment or variant thereof.

The subject invention also concerns methods of treating Alzheimer's disease, cerebral amyloid angiopathy, cerebrovascular disease in the presence of Alzheimer's disease, or traumatic brain injury, by inhibiting or antagonizing the anti-angiogenic activity of the Aβ peptide within a patient. The anti-angiogenic activity of the Aβ peptide can be inhibited, for example, by suppressing the functional expression of the Aβ peptide or by administering a compound that inhibits the anti-angiogenic activity of the Aβ peptide. In one embodiment, the compound that inhibits the anti-angiogenic activity of the Aβ peptide is a trophic factor, such as vascular endothelial growth factor (VEGF), endothelial growth factor (EGF), platelet-derived growth factor (PDGF), or neural growth factor (NGF). In another aspect, the subject invention provides methods for identifying compounds for the treatment of Alzheimer's disease by evaluating a candidate compound for its effect on the anti-angiogenic activity of the Aβ peptide.

Various methods known in the art for suppressing the functional expression of a gene can be utilized to carry out this method of the subject invention. The amyloid precursor protein (APP) gene or the nucleic acid encoding the Aβ peptide can be disrupted partially (e.g., a leaky mutation), resulting, for example, in reduced expression, or the APP gene or Aβ nucleic acid can be fully disrupted (e.g., complete gene ablation). Such mutations can include, for example, point mutations, such as transitions or transversions, or insertions and/or deletions, and the mutation can occur in the coding region encoding Aβ or merely in its regulatory sequences. According to the method of the subject invention, functional expression of the gene encoding the Aβ peptide can be suppressed at any level. In another aspect, the subject invention includes methods of disrupting expression of the gene encoding the Aβ peptide, or a biologically active fragment or variant thereof, in vivo or in vitro.

Various means for suppression of the Aβ peptide's anti-angiogenic function can be utilized according to the method of the subject invention. For example, suppression of Aβ peptide function can be carried out by administration of an agent that directly or indirectly causes suppression of Aβ peptide function. Agents suitable for the method of the subject invention include nucleic acids, such as a genetic construct or other genetic means for directing expression of an antagonist of Aβ peptide anti-angiogenic function. Nucleic acid molecules suitable for the method of the invention include, for example, anti-sense polynucleotides, or other polynucleotides that bind to Aβ peptide mRNA, for example. Other agents that can be utilized to carry out suppression of Aβ peptide's anti-angiogenic function include, for example, peptidomimetics, ribozymes, and RNA aptamers.

According to the method of the subject invention, polypeptides can be administered to a patient in order to suppress Aβ peptide function, which alleviates or prevents the symptom of Alzheimer's disease.

In another aspect of the invention, Aβ peptide, or biologically active fragments or variants of the Aβ peptide, are administered to a patient in order to increase Aβ peptide's anti-angiogenic function. Preferably, the polypeptides utilized are those disclosed herein. The polypeptides can comprise fragments of the full-length Aβ peptide amino acid sequence (including fragments of full-length amino acid sequences of Aβ peptide homologs). For example, the polypeptides can comprise amino acid sequences corresponding to:

the Aβ$_{1-43}$ peptide (H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Thr-OH) (SEQ ID NO. 1);

the Aβ$_{1-42}$ peptide (H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH) (SEQ ID NO. 2); and the Aβ$_{1-40}$ peptide (H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH) (SEQ ID NO. 3).

Other Aβ peptides that can be used according to the subject invention include, for example:

the 21G-Aβ$_{1-42}$ (Flemish) mutant peptide (H$_2$N-Asp-Ala-Glu-Phe-Arg-His-Asp-Ser-Gly-Tyr-Glu-Val-His-His-Gln-Lys-Leu-Val-Phe-Phe-Gly-Glu-Asp-Val-Gly-Ser-Asn-Lys-Gly-Ala-Ile-Ile-Gly-Leu-Met-Val-Gly-Gly-Val-Val-Ile-Ala-OH) (SEQ ID NO. 7) (Hendriks, L. et al., *Nature Genet.*, 11:218-221, 1992);

the 22Q-Aβ$_{1-42}$ (Dutch) mutant peptide (H$_2$N-Asp-Ala-Glu-Phe-Arg-His-Asp-Ser-Gly-Tyr-Glu-Val-His-His-Gln-Lys-Leu-Val-Phe-Phe-Ala-Gln-Asp-Val-Gly-Ser-Asn-Lys-Gly-Ala-Ile-Ile-Gly-Leu-Met-Val-Gly-Gly- Val-Val-Ile-Ala-OH) (SEQ ID NO. 8) (Levy, E. et al., *Science*, 248:1124-1126, 1990);

the 22K-A$\beta_{1-42}$ (Italian) mutant peptide (H$_2$N-Asp-Ala-Glu-Phe-Arg-His-Asp-Ser-Gly-Tyr-Glu-Val-His-His-Gln-Lys-Val-Phe-Phe-Ala-Lys-Asp-Val-Gly-Ser-Asn-Lys-Gly-Ala-Ile-Ile-Gly-Leu-Met-Val-Gly-Gly-Val-Val-Ile-Ala-OH) (SEQ ID NO. 9) (Miravalle, L. et al., *J. Biol. Chem.*, 275:27110-27116, 2000);

the 22G-A$\beta_{1-42}$ (Arctic) mutant peptide (H$_2$N-Asp-Ala-Glu-Phe-Arg-His-Asp-Ser-Gly-Tyr-Glu-Val-His-His-Gln-Lys-Leu-Val-Phe-Phe-Ala-Gly-Asp-Val-Gly-Ser-Asn-Lys-Gly-Ala-Ile-Ile-Gly-Leu-Met-Val-Gly-Gly-Val-Val-Ile-Ala-OH) (SEQ ID NO. 10) (Nilsberth, C. et al., *Nature Neurosci.*, 4:887-893, 2001)

the 23N-A$\beta_{1-42}$ (Iowa) mutant peptide (H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asn-Val-Gly-Ser-Asn-Lys-Gly-Ala-Ile-Ile-Gly-Leu-Met-Val-Gly-Gly-Val-Val-Ile-Ala-OH) (SEQ ID NO. 11) (Grabowski, T. J. et al., *Ann. Neurol.*, 49:697-705, 2001).

In one embodiment, biologically active variants of the A$\beta_{1-42}$ peptide (SEQ ID NO. 2) are utilized, wherein the variants have a substitution at the 21 amino acid position, or the 22 amino acid position, or 23 amino acid position, or combinations thereof. In a specific embodiment, the substitution(s) is a conservative substitution which does not materially alter the biological activity of the polypeptide.

Various means for delivering polypeptides to a cell can be utilized to carry out the methods of the subject invention. For example, protein transduction domains (PTDs) can be fused to the polypeptide, producing a fusion polypeptide, in which the PTDs are capable of transducing the polypeptide cargo across the plasma membrane (Wadia, J. S. and Dowdy, S. F., *Curr. Opin. Biotechnol.*, 2002, 13(1)52-56). Examples of PTDs include the Drosophila homeotic transcription protein antennapedia (Antp), the herpes simples virus structural protein VP22, and the human immuno-deficiency virus 1 (HIV-1) transcriptional activator Tat protein.

According to the method of angiogenesis inhibition of the subject invention, recombinant cells can be administered to a patient, wherein the recombinant cells have been genetically modified to express an A$\beta$ gene product, such as the amino acid sequences set forth in SEQ ID NO. 1, SEQ ID NO. 2, SEQ ID NO. 3, SEQ ID NO. 7, SEQ ID NO. 8, SEQ ID NO. 9, SEQ ID NO. 10, SEQ ID NO. 11, or biologically active fragments or variants thereof. If the cells to be genetically modified already express an A$\beta$ gene product, the genetic modification can serve to enhance or increase expression of the A$\beta$ gene product beyond the normal or constitutive amount (e.g., "overexpression").

The method of angiogenesis inhibition of the subject invention can be used to treat a patient suffering from cancer, or as a cancer preventative. The method of tumor inhibition of the subject invention can be used to treat patients suffering from a variety of cancers including, but not limited to cancer of the breast, prostate, melanoma, chronic myelogenous leukemia, cervical cancer, adenocarcinoma, lymphoblastic leukemia, colorectal cancer, and lung carcinoma. According to the methods of the subject invention, various other anti-cancer or anti-tumor compounds, such as cytotoxic agents, can be administered in conjunction with (before, during, or after) increasing the in vivo concentrations of an A$\beta$ peptide.

In another aspect, the subject invention provides isolated and/or purified nucleotide sequences comprising: (i) a polynucleotide sequence encoding the amino acid sequence set forth in SEQ ID NO. 1, SEQ ID NO. 2, SEQ ID NO. 3, SEQ ID NO. 7, SEQ ID NO. 8, SEQ ID NO. 9, SEQ ID NO. 10, SEQ ID NO. 11, or a complement thereof; (ii) a polynucleotide sequence having at least about 20% to 99.99% identity to the polynucleotide sequence of (i); (iii) a polynucleotide encoding a fragment of the amino acid sequence shown in SEQ ID NO. 1, SEQ ID NO. 2, SEQ ID NO. 3, SEQ ID NO. 7, SEQ ID NO. 8, SEQ ID NO. 9, SEQ ID NO. 10, SEQ ID NO. 11; or (iv) an interfering RNA sequence corresponding to the transcript of the polynucleotide set forth in SEQ ID NO. 6, or a fragment of the transcript.

Nucleotide, polynucleotide, or nucleic acid sequences(s) are understood to mean, according to the present invention, either a double-stranded DNA, a single-stranded DNA, or products of transcription of the said DNAs (e.g., RNA molecules). It should also be understood that the present invention does not relate to the genomic nucleotide sequences encoding A$\beta$ peptide in their natural/native environment or natural/native state. The nucleic acid, polynucleotide, or nucleotide sequences of the invention have been isolated, purified (or partially purified), by separation methods including, but not limited to, ion-exchange chromatography, molecular size exclusion chromatography, affinity chromatography, or by genetic engineering methods such as amplification, cloning or subcloning.

Optionally, the polynucleotide sequences of the instant invention can also contain one or more polynucleotides encoding heterologous polypeptide sequences (e.g., tags that facilitate purification of the polypeptides of the invention (see, for example, U.S. Pat. No. 6,342,362, hereby incorporated by reference in its entirety; Altendorf et al. [1999-WWW, 2000] "Structure and Function of the F$_o$ Complex of the ATP Synthase from *Escherichia Coli*," *J. of Experimental Biology* 203:19-28, The Co. of Biologists, Ltd., G. B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al [1995] "Current Trends in Molecular Recognition and Bioseparation," *J. of Chromatography A*. 707:3-22, Elsevier Science B.V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: the Strep-tag", *Biomolecular Engineering* 16:79-86, Elsevier Science, B.V.; Smith [1998] "Cookbook for Eukaryotic Protein Expression: Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology*, 139:49-57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or INVITROGEN (San Diego, Calif.).

Other aspects of the invention provide vectors containing one or more of the polynucleotides of the invention, such as vectors containing nucleotides encoding the Aβ peptide or biologically active fragments or variants of the Aβ peptide. The vectors can be vaccine, replication, or amplification vectors. In some embodiments of this aspect of the invention, the polynucleotides are operably associated with regulatory elements capable of causing the expression of the polynucleotide sequences. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations of the aforementioned vector sources, such as those derived from plasmid and bacteriophage genetic elements (e.g., cosmids and phagemids).

As indicated above, vectors of this invention can also comprise elements necessary to provide for the expression and/or the secretion of a polypeptide, such as the Aβ peptide, or a biologically active fragment or variant thereof, encoded by the nucleotide sequences of the invention in a given host cell. The vector can contain one or more elements selected from the group consisting of a promoter, signals for initiation of translation, signals for termination of translation, and appropriate regions for regulation of transcription. In certain embodiments, the vectors can be stably maintained in the host cell and can, optionally, contain signal sequences directing the secretion of translated protein. Other embodiments provide vectors that are not stable in transformed host cells. Vectors can integrate into the host genome or be autonomously-replicating vectors.

In a specific embodiment, a vector comprises a promoter operably linked to a protein or peptide-encoding nucleic acid sequence, one or more origins of replication, and, optionally, one or more selectable markers (e.g., an antibiotic resistance gene). Non-limiting exemplary vectors for the expression of the polypeptides of the invention include pBr-type vectors, pET-type plasmid vectors (PROMEGA), pBAD plasmid vectors (INVITROGEN) or those provided in the examples below. Furthermore, vectors according to the invention are useful for transforming host cells for the cloning or expression of the nucleotide sequences of the invention.

Promoters which may be used to control expression include, but are not limited to, the CMV promoter, the SV40 early promoter region (Bernoist and Chambon [1981] *Nature* 290:304-310), the promoter contained in the 3' long terminal repeat of Rous sarcoma virus (Yamamoto, et al. [1980] *Cell* 22:787-797), the herpes thymidine kinase promoter (Wagner et al. [1981] *Proc. Natl. Acad. Sci. USA* 78:1441-1445), the regulatory sequences of the metallothionein gene (Brinster et al. [1982] *Nature* 296:39-42); prokaryotic vectors containing promoters such as the β-lactamase promoter (Villa-Kamaroff, et al. [1978] *Proc. Natl. Acad. Sci. USA* 75:3727-3731), or the tac promoter (DeBoer, et al. [1983] *Proc. Natl. Acad. Sci. USA* 80:21-25); see also, "Useful Proteins from Recombinant Bacteria" in *Scientific American,* 1980, 242:74-94; plant expression vectors comprising the nopaline synthetase promoter region (Herrera-Estrella et al. [1983] *Nature* 303:209-213) or the cauliflower mosaic virus 35S RNA promoter (Gardner, et al. [1981] *Nucl. Acids Res.* 9:2871), and the promoter of the photosynthetic enzyme ribulose biphosphate carboxylase (Herrera-Estrella et al. [1984] *Nature* 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The subject invention also provides for "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acid to the polynucleotides of the invention provide for "homologous" or "modified" nucleotide sequences. In various embodiments, "homologous" or "modified" nucleic acid sequences have substantially the same biological or serological activity as the native (naturally occurring) Aβ peptide. A "homologous" or "modified" nucleotide sequence will also be understood to mean a splice variant of the polynucleotides of the instant invention or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% (inclusive). The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman [1988] *Proc. Natl. Acad. Sci. USA* 85(8):2444-2448; Altschul et al. [1990] *J. Mol. Biol.* 215(3):403-410; Thompson et al. [1994] *Nucleic Acids Res.* 22(2):4673-4680; Higgins et al. [1996] *Methods Enzymol.* 266:383-402; Altschul et al. [1990] *J. Mol. Biol.* 215(3):403-410; Altschul et al. [1993] *Nature Genetics* 3:266-272).

The subject invention also provides nucleotide sequences complementary to any of the polynucleotide sequences disclosed herein. Thus, the invention is understood to include any DNA whose nucleotides are complementary to those of the sequence of the invention, and whose orientation is reversed (e.g., an antisense sequence).

The present invention further provides fragments of the polynucleotide sequences provided herein. Representative fragments of the polynucleotide sequences according to the invention will be understood to mean any nucleotide fragment having at least 8 or 9 successive nucleotides, preferably at least 12 successive nucleotides, and still more preferably at least 15 or at least 20 successive nucleotides of the sequence from which it is derived. The upper limit for such fragments is the total number of polynucleotides found in the full-length sequence (or, in certain embodiments, of the full length open reading frame (ORF) identified herein). It is understood that such fragments refer only to portions of the disclosed polynucleotide sequences that are not listed in a publicly available database or prior art references. However, it should be understood that with respect to the method for inhibiting angiogenesis of the subject invention, disclosed nucleotides (and polypeptides encoded by such nucleotides) that are listed in a publicly available database or prior art reference can also be utilized. For example, nucleotide sequences that are Aβ peptide homologs, or fragments thereof, which have been previously identified, can be utilized to carry out the method for inhibiting angiogenesis of the subject invention.

In other embodiments, fragments contain from one nucleotide less than the full length Aβ polynucleotide sequence (129 nucleotides) to fragments comprising up to, and including 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, and up to 128 consecutive nucleotides of a particular nucleotide disclosed herein or encoding a particular polypeptide disclosed herein.

Among these representative fragments, those capable of hybridizing under stringent conditions with a nucleotide sequence according to the invention are preferred. Conditions of high or intermediate stringency are provided infra and are chosen to allow for hybridization between two complementary DNA fragments. Hybridization conditions for a polynucleotide of about 300 bases in size will be adapted by persons skilled in the art for larger- or smaller-sized oligonucleotides, according to methods well known in the art (see, for example, Sambrook et al. [1989] *Molecular Cloning, A Laboratory Manual, Second Edition*, Cold Spring Harbor Press, N.Y., pp. 9.47-9.57).

The subject invention also provides detection probes (e.g., fragments of the disclosed polynucleotide sequences) for hybridization with a target sequence or an amplicon generated from the target sequence. Such a detection probe will advantageously have as sequence a sequence of at least 9, 12, 15, 20, 25, 30, 35, 40, 45, 50, 55, 60, 65, 70, 75, 80, 85, 90, 95, or 100 nucleotides. Alternatively, detection probes can comprise 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127 and up to, for example, 128 consecutive nucleotides of the disclosed nucleic acids. The detection probes can also be used as labeled probe or primer in the subject invention. Labeled probes or primers are labeled with a radioactive compound or with another type of label. Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

The nucleotide sequences according to the invention may also be used in analytical systems, such as DNA chips. DNA chips and their uses are well known in the art and (see for example, U.S. Pat. Nos. 5,561,071; 5,753,439; 6,214,545; Schena et al. [1996] *BioEssays* 18:427-431; Bianchi et al. [1997] *Clin. Diagn. Virol.* 8:199-208; each of which is hereby incorporated by reference in their entireties) and/or are provided by commercial vendors such as AFFYMETRIX, Inc. (Santa Clara, Calif.).

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak [1987] *DNA Probes*, Stockton Press, New York, N.Y., pp. 169-170.

By way of example, hybridization of immobilized DNA on Southern blots with $^{32}P$-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$T_m = 81.5°$ C. $+ 16.6$ Log [Na+]$+0.41(\%G+C)-0.61(\%$ formamide)$-600$/length of duplex in base pairs.

Washes are typically carried out as follows:
(1) twice at room temperature for 15 minutes in 1×SSPE, 0.1% SDS (low stringency wash);
(2) once at $T_m-20°$ C. for 15 minutes in 0.2×SSPE, 0.1% SDS (moderate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$T_m$(° C.)$=2$(number T/A base pairs)$+4$(number G/C base pairs) (Suggs et al. [1981] *J ICN-UCLA Symp. Dev. Biol. Using Purified Genes*, D. D. Brown [ed.], Academic Press, New York, 23:683-693).

Washes can be carried out as follows:
(1) twice at room temperature for 15 minutes 1×SSPE, 0.1% SDS (low stringency wash;
(2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2X SSPE, room temperature
Low: 1 or 2X SSPE, 42° C.
Moderate: 0.2X or 1X SSPE, 65° C.
High: 0.1X SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art (see, for example, Sambrook et al. [1989] *Molecular Cloning, A Laboratory Manual, Second Edition*, Cold Spring Harbor Press, N.Y., pp. 9.47-9.57; and Ausubel et al. [1989] *Current Protocols in Molecular Biology*, Green Publishing Associates and Wiley Interscience, N.Y., each incorporated herein in its entirety).

A further non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art (see, for example, Sambrook et al. [1989] *Molecular Cloning, A Laboratory Manual, Second Edition*, Cold Spring Harbor Press, N.Y., pp. 9.47-9.57; and Ausubel et al [1989] *Current Protocols in Molecular Biology*, Green Publishing Associates and Wiley Interscience, N.Y., each of which is incorporated herein in its entirety).

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006-13512. The nucleic acid sequences of the subject invention can also be used as molecular weight markers in nucleic acid analysis procedures.

The invention also provides host cells transformed by a polynucleotide according to the invention and the production of Aβ peptide, or a biologically active fragment or variant thereof, by the transformed host cells. In some embodiments, transformed cells comprise an expression vector containing Aβ polynucleotide sequences, or a biologically active fragment or variant thereof. Other embodiments provide for host cells transformed with nucleic acids. Yet other embodiments provide transformed cells comprising an expression vector containing fragments of Aβ polynucleotide sequences. Transformed host cells according to the invention are cultured under conditions allowing the replication and/or the expression of the nucleotide sequences of the invention. Expressed polypeptides are recovered from culture media and purified, for further use, according to methods known in the art.

The host cell may be chosen from eukaryotic or prokaryotic systems, for example bacterial cells (Gram negative or Gram positive), yeast cells, animal cells, plant cells, and/or insect cells using baculovirus vectors. In some embodiments, the host cell for expression of the polypeptides include, and are not limited to, those taught in U.S. Pat. Nos. 6,319,691; 6,277,375; 5,643,570; 5,565,335; Unger [1997] *The Scientist* 11(17):20; or Smith [1998] *The Scientist* 12(22):20, each of which is incorporated by reference in its entirety, including all references cited within each respective patent or reference. Other exemplary, and non-limiting, host cells include *Staphylococcus* spp., *Enterococcus* spp., *E. coli*, and *Bacillus subtilis*; fungal cells, such as *Streptomyces* spp., *Aspergillus* spp., *S. cerevisiae, Schizosaccharomyces pombe, Pichia pastoris, Hansela polymorpha, Kluveromyces lactis*, and *Yarrowia lipolytica*; insect cells such as Drosophila S2 and Spodoptera Sf9 cells; animal cells such as CHO, COS, HeLa, C127, 3T3, BHK, 293 and Bowes melanoma cells; and plant cells. A great variety of expression systems can be used to produce the polypeptides of the invention and polynucleotides can be modified according to methods known in the art to provide optimal codon usage for expression in a particular expression system.

Furthermore, a host cell strain may be chosen that modulates the expression of the inserted sequences, modifies the gene product, and/or processes the gene product in the specific fashion. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product whereas expression in yeast will produce a glycosylated product. Expression in mammalian cells can be used to provide "native" glycosylation of a heterologous protein. Furthermore, different vector/host expression systems may effect processing reactions to different extents.

Nucleic acids and/or vectors can be introduced into host cells by well-known methods, such as, calcium phosphate transfection, DEAE-dextran mediated transfection, transfection, microinjection, cationic lipid-mediated transfection, electroporation, transduction, scrape loading, ballistic introduction and infection (see, for example, Sambrook et al. [1989] *Molecular Cloning: A Laboratory Manual*, 2$^{nd}$ Ed., Cold Spring Harbor Laboratory Press, Cold Spring Harbor, N.Y.).

The subject invention also provides for the expression of a polypeptide, derivative, or a variant (e.g., a splice variant) encoded by a polynucleotide sequence disclosed herein. Alternatively, the invention provides for the expression of a polypeptide fragment obtained from a polypeptide, derivative, or a variant encoded by a polynucleotide fragment derived from the polynucleotide sequences disclosed herein. In either embodiment, the disclosed sequences can be regulated by a second nucleic acid sequence so that the polypeptide or fragment is expressed in a host transformed with a recombinant DNA molecule according to the subject invention. For example, expression of a protein or peptide may be controlled by any promoter/enhancer element known in the art.

The subject invention also provides nucleic acid-based methods for the identification of the presence of the Aβ gene, or fragments or variants thereof, in a sample. These methods can utilize the nucleic acids of the subject invention and are well known to those skilled in the art (see, for example, Sambrook et al. [1989] *Molecular Cloning, A Laboratory Manual, Second Edition*, Cold Spring Harbor Press, N.Y., pp. 9.47-9.57, or Abbaszadega [2001] "Advanced Detection of Viruses and Protozoan Parasites in Water," *Reviews in Biology and Biotechnology*, 1(2):21-26). Among the techniques useful in such methods are enzymatic gene amplification (or PCR), Southern blots, Northern blots, or other techniques utilizing nucleic acid hybridization for the identification of polynucleotide sequences in a sample. The nucleic acids can be used to screen individuals for disorders associated with dysregulation of the Aβ gene or its transcriptional products.

The subject invention also provides polypeptides encoded by nucleotide sequences of the invention. The subject invention also provides fragments of at least 5 amino acids of a polypeptide encoded by the polynucleotides of the instant invention.

In the context of the instant invention, the terms polypeptide, peptide and protein are used interchangeably. Likewise, the terms variant and homologous are also used interchangeably. It should be understood that the invention does not relate to the polypeptides in natural form or native environment. Peptides and polypeptides according to the invention have been isolated or obtained by purification from natural sources (or their native environment), chemically synthesized, or obtained from host cells prepared by genetic manipulation (e.g., the polypeptides, or fragments thereof, are recombinantly produced by host cells). Polypeptides according to the instant invention may also contain non-natural amino acids, as will be described below.

"Variant" or "homologous" polypeptides will be understood to designate the polypeptides containing, in relation to the native polypeptide, modifications such as deletion, addition, or substitution of at least one amino acid, truncation, extension, or the addition of chimeric heterologous polypeptides. Optionally, "variant" or "homologous" polypeptides can contain a mutation or post-translational modifications. Among the "variant" or "homologous" polypeptides, those whose amino acid sequence exhibits 20.00% to 99.99% (inclusive) identity to the native polypeptide sequence are preferred. The aforementioned range of percent identity is to be taken as including, and providing written description and support for, any fractional percentage, in intervals of 0.01%, between 50.00% and, up to, including 99.99%. These percentages are purely statistical and differences between two polypeptide sequences can be distributed randomly and over the entire sequence length.

"Variant" or "homologous" polypeptide sequences exhibiting a percentage identity with the polypeptides of the present invention can, alternatively, have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 91, 82, 83, 84, 85, 86, 87, 88, 89, 90, 91, 92, 93, 94, 95, 96, 97, 98, or 99 percent identity with the polypeptide sequences of the instant invention. The expression equivalent amino acid is intended here to designate any amino acid capable of being substituted for one of the amino acids in the basic structure without, however, essentially modifying the biological activities of the corresponding peptides and as provided below.

By way of example, amino acid substitutions can be carried out without resulting in a substantial modification of the biological activity of the corresponding modified polypeptides; for example, the replacement of leucine with valine or isoleucine; aspartic acid with glutamic acid; glutamine with asparagine; arginine with lysine; and the reverse substitutions can be performed without substantial modification of the biological activity of the polypeptides.

In other embodiments, homologous polypeptides according to the subject invention also include various splice variants identified within the Aβ coding sequence.

The subject invention also provides biologically active fragments of a polypeptide according to the invention and includes those peptides capable of eliciting an immune response. The immune response can provide components (either antibodies or components of the cellular immune response (e.g., B-cells, helper, cytotoxic, and/or suppressor T-cells) reactive with the biologically active fragment of a polypeptide, the intact, full length, unmodified polypeptide disclosed herein, or both the biologically active fragment of a polypeptide and the intact, full length, unmodified polypeptides disclosed herein.

Biologically active fragments according to the invention comprise from five (5) amino acids to one amino acid less than the full length of any polypeptide sequence provided herein. Alternatively, fragments comprising 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, and up to 43 consecutive amino acids of a disclosed polypeptide sequence are provided herein.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector containing nucleic acids encoding polypeptide fragments according to the invention. The transformed host cells contain a nucleic acid and are cultured according to well-known methods; thus, the invention allows for the expression of these fragments, under the control of appropriate elements for regulation and/or expression of the polypeptide fragments.

Modified polypeptides according to the invention are understood to designate a polypeptide obtained by variation in the splicing of transcriptional products of the Aβ gene, genetic recombination, or by chemical synthesis as described below. Modified polypeptides contain at least one modification in relation to the normal polypeptide sequence. These modifications can include the addition, substitution, deletion of amino acids contained within the polypeptides of the invention.

Conservative substitutions whereby an amino acid of one class is replaced with another amino acid of the same type fall within the scope of the subject invention so long as the substitution does not materially alter the biological activity of the polypeptide. For example, the class of nonpolar amino acids include Ala, Val, Leu, Ile, Pro, Met, Phe, and Trp; the class of uncharged polar amino acids includes Gly, Ser, Thr, Cys, Tyr, Asn, and Gln; the class of acidic amino acids includes Asp and Glu; and the class of basic amino acids includes Lys, Arg, and His. In some instances, non-conservative substitutions can be made where these substitutions do not significantly detract from the biological activity of the polypeptide.

In order to extend the life of the polypeptides of the invention, it may be advantageous to use non-natural amino acids, for example in the D form, or alternatively amino acid analogs, such as sulfur-containing forms of amino acids. Alternative means for increasing the life of polypeptides can also be used in the practice of the instant invention. For example, polypeptides of the invention, and fragments thereof, can be recombinantly modified to include elements that increase the plasma, or serum half-life of the polypeptides of the invention. These elements include, and are not limited to, antibody constant regions (see for example, U.S. Pat. No. 5,565,335, hereby incorporated by reference in its entirety, including all references cited therein), or other elements such as those disclosed in U.S. Pat. Nos. 6,319,691; 6,277,375; or 5,643,570, each of which is incorporated by reference in its entirety, including all references cited within each respective patent. Alternatively, the polynucleotides and genes of the instant invention can be recombinantly fused to elements that are useful in the preparation of immunogenic constructs for the purposes of vaccine formulation or elements useful for the isolation of the polypeptides of the invention.

The polypeptides, fragments, and immunogenic fragments of the invention may further contain linkers that facilitate the attachment of the fragments to a carrier molecule for delivery or diagnostic purposes. The linkers can also be used to attach fragments according to the invention to solid support matrices for use in affinity purification protocols. In this aspect of the invention, the linkers specifically exclude, and are not to be considered anticipated, where the fragment is a subsequence of another peptide, polypeptide, or protein as identified in a search of protein sequence databases as indicated in the preceding paragraph. In other words, the non-identical portions of the other peptide, polypeptide, of protein is not considered to be a "linker" in this aspect of the invention. Non-limiting examples of "linkers" suitable for the practice of the invention include chemical linkers (such as those sold by Pierce, Rockford, Ill.), peptides that allow for the connection of the immunogenic fragment to a carrier molecule (see, for example, linkers disclosed in U.S. Pat. Nos. 6,121,424; 5,843,464; 5,750,352; and 5,990,275, hereby incorporated by reference in their entirety). In various embodiments, the linkers can be up to 50 amino acids in length, up to 40 amino acids in length, up to 30 amino acids in length, up to 20 amino acids in length, up to 10 amino acids in length, or up to 5 amino acids in length.

In other specific embodiments, the polypeptides, peptides, derivatives, or analogs thereof may be expressed as a fusion, or chimeric protein product (comprising the protein, fragment, analog, or derivative joined via a peptide bond to a heterologous protein sequence (e.g., a different protein)). Such a chimeric product can be made by ligating the appropriate nucleic acid sequences encoding the desired amino acid sequences to each other by methods known in the art, in the proper coding frame, and expressing the chimeric product by methods commonly known in the art (see, for example, U.S. Pat. No. 6,342,362, hereby incorporated by reference in its entirety; Altendorf et al. [1999-WWW, 2000] "Structure and Function of the $F_0$ Complex of the ATP Synthase from *Escherichia Coli,*" *J. of Experimental* Biology 203:19-28, The Co. of Biologists, Ltd., G.B.; Baneyx [1999] "Recombinant Protein Expression in *Escherichia coli,*" Biotechnology 10:411-21, Elsevier Science Ltd.; Eihauer et al [2001] "The FLAG™ Peptide, a Versatile Fusion Tag for the Purification of Recombinant Proteins," *J. Biochem Biophys Methods* 49:455-65; Jones et al. [1995 ] *J. Chromatography* 707:3-22; Jones et al. [1995] "Current Trends in Molecular Recognition and Bioseparation," *J. Chromatography A.* 707:3-22, Elsevier Science B.V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," *TibTech* 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: The Strep-tag", *Biomolecular Engineering* 16:79-86, Elsevier Science, B.V.; Smith [1998] "Cookbook for Eukaryotic Protein Expression: Yeast, Insect, and Plant Expression Systems," The Scientist 12(22):20; Smyth et al. [2000] "Eukaryotic Expression and Purification of Recombinant Extracellular Matrix Proteins Carrying the Strep II Tag", *Methods in Molecular Biology,* 139:49-57; Unger [1997] "Show Me the Money: Prokaryotic Expression Vectors and Purification Systems," *The Scientist* 11(17):20, each of which is hereby incorporated by reference in their entireties). Alternatively, such a chimeric product may be made by protein synthetic techniques, e.g., by use of a peptide synthesizer. Fusion peptides can comprise polypeptides of the subject invention and one or more protein transduction domains, as described above. Such fusion peptides are particularly useful for delivering the cargo polypeptide through the cell membrane.

Increasing the amount of Aβ peptide activity within a tissue is useful in treating a variety of angiogenic diseases, such as cancers, tumors, and/or malignancies. Thus, according to the methods of the subject invention, the amount of Aβ peptide activity can be increased within a tissue by directly administering the Aβ peptide to a patient suffering from an angiogenic disease (such as exogenous delivery of the Aβ peptide) or by indirect or genetic means (such as delivery of a polynucleotide encoding the Aβ peptide or upregulating the endogenous Aβ peptide activity). Non-limiting examples of such cancers, tumors, and/or malignancies that can be treated using the methods of the invention include prostate cancer, breast cancer, melanoma, chronic myelogenous leukemia, cervical cancer, adenocarcinomas, lymphoblastic leukemia, colorectal cancer, and lung carcinoma. Accordingly, the present invention provides a method for screening, or aiding in the diagnosis of, an individual suspected of having an angiogenic or angiogenesis-mediated disease. The subject invention provides methods comprising the steps of determining the amount of Aβ peptide in a biological sample obtained from an individual and comparing the measured amount of Aβ peptide to the amount of Aβ found in the normal population. The presence of a significantly increased amount of Aβ peptide is associated with an indication of Alzheimer's disease. The presence of a significantly decreased amount of Aβ peptide is associated with an indication of an angiogenic disease, such as a malignancy or cancer. Aβ peptide gene product can be detected by well-known methodologies including, and not limited to, Western blots, enzyme linked immunoassays (ELISAs), radioimmunoassays (RIAs), Northern blots, Southern blots, PCR-based assays, or other assays for the quantification of gene product known to the skilled artisan. This information, in conjunction with other information available to the skilled practitioner, assists in making a diagnosis.

Antisense technology can also be used to interfere with expression of the disclosed polynucleotides encoding Aβ peptides. For example, the transformation of a cell or organism with the reverse complement of a gene encoded by a polynucleotide exemplified herein can result in strand co-suppression and silencing or inhibition of a target gene, e.g., one involved in the infection process.

Polynucleotides disclosed herein are useful as target genes for the synthesis of antisense RNA or dsRNA useful for RNA-mediated gene interference. The ability to specifically inhibit gene function in a variety of organisms utilizing antisense RNA or dsRNA-mediated interference is well known in the fields of molecular biology (see for example C. P. Hunter, Current Biology [1999] 9:R440-442; Hamilton et al., [1999] Science, 286:950-952; and S. W. Ding, Current Opinions in Biotechnology [2000] 11:152-156, hereby incorporated by reference in their entireties). dsRNA (RNAi) typically comprises a polynucleotide sequence identical or homologous to a target gene (or fragment thereof) linked directly, or indirectly, to a polynucleotide sequence complementary to the sequence of the target gene (or fragment thereof). The dsRNA may comprise a polynucleotide linker sequence of sufficient length to allow for the two polynucleotide sequences to fold over and hybridize to each other; however, a linker sequence is not necessary. The linker sequence is designed to separate the antisense and sense strands of RNAi significantly enough to limit the effects of steric hindrances and allow for the formation of dsRNA molecules and should not hybridize with sequences within the hybridizing portions of the dsRNA molecule. The specificity of this gene silencing mechanism appears to be extremely high, blocking expression only of targeted genes, while leaving other genes unaffected. Accordingly, one method for controlling gene expression according to the subject invention provides materials and methods using double-stranded interfering RNA (dsRNAi), or RNA-mediated interference (RNAi). The terms "dsRNAi", "RNAi", "iRNA", and "siRNA" are used interchangeably herein unless otherwise noted.

RNA containing a nucleotide sequence identical to a fragment of the target gene is preferred for inhibition; however, RNA sequences with insertions, deletions, and point mutations relative to the target sequence can also be used for inhibition. Sequence identity may optimized by sequence comparison and alignment algorithms known in the art (see Gribskov and Devereux, *Sequence Analysis Primer*, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a fragment of the target gene transcript.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands); the promoters may be known inducible promoters such as baculovirus. Inhibition may be targeted by specific transcription in an organ, tissue, or cell type. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874; 5,698,425; 5,712,135; 5,789,214; and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no, or a minimum of, purification to avoid losses due to sample processing. The RNA may be dried for storage or dissolved in an aqueous solution. The solution may contain buffers or salts to promote annealing, and/or stabilization of the duplex strands.

Preferably and most conveniently, dsRNAi can be targeted to an entire polynucleotide sequence set forth herein. Preferred RNAi molecules of the instant invention are highly homologous or identical to the polynucleotides of the sequence listing. The homology may be greater than 70%, preferably greater than 80%, more preferably greater than 90% and is most preferably greater than 95%.

Fragments of genes can also be utilized for targeted suppression of gene expression. These fragments are typically in the approximate size range of about 20 nucleotides. Thus, targeted fragments are preferably at least about 15 nucleotides. In certain embodiments, the gene fragment targeted by the RNAi molecule is about 20-25 nucleotides in length. In a more preferred embodiment, the gene fragments are at least about 25 nucleotides in length. In an even more preferred embodiment, the gene fragments are at least 50 nucleotides in length.

Thus, RNAi molecules of the subject invention are not limited to those that are targeted to the full-length polynucleotide or gene. Gene product can be inhibited with an RNAi molecule that is targeted to a portion or fragment of the exemplified polynucleotides; high homology (90-95%) or greater identity is also preferred, but not necessarily essential, for such applications.

In another aspect of the invention, the dsRNA molecules of the invention may be introduced into cells with single stranded (ss) RNA molecules which are sense or anti-sense RNA derived from the nucleotide sequences disclosed herein. Methods of introducing ssRNA and dsRNA molecules into cells are well-known to the skilled artisan and includes transcription of plasmids, vectors, or genetic constructs encoding the ssRNA or dsRNA molecules according to this aspect of the invention; electroporation, biolistics, or other well-known methods of introducing nucleic acids into cells may also be used to introduce the ssRNA and dsRNA molecules of this invention into cells.

As used herein, the term "administration" or "administering" refers to the process of delivering an agent to a patient, wherein the agent directly or indirectly modulates (enhances or inhibits) Aβ peptide function. The process of administration can be varied, depending on the agent, or agents, and the desired effect. Administration can be accomplished by any means appropriate for the therapeutic agent, for example, by parenteral, mucosal, pulmonary, topical, catheter-based, or oral means of delivery. Parenteral delivery can include for example, subcutaneous intravenous, intrauscular, intra-arterial, and injection into the tissue of an organ, particularly tumor tissue. Mucosal delivery can include, for example, intranasal delivery. Oral or intranasal delivery can include the administration of a propellant. Pulmonary delivery can include inhalation of the agent. Catheter-based delivery can include delivery by iontropheretic catheter-based delivery. Oral delivery can include delivery of a coated pill, or administration of a liquid by mouth. Administration can generally also include delivery with a pharmaceutically acceptable carrier, such as, for example, a buffer, a polypeptide, a peptide, a polysaccharide conjugate, a liposome, and/or a lipid. Gene therapy protocol is also considered an administration in which the therapeutic agent is a polynucleotide capable of accomplishing a therapeutic goal when expressed as a transcript or a polypeptide into the patient.

The pharmaceutical compositions of the subject invention can be formulated according to known methods for preparing pharmaceutically useful compositions. Formulations are described in a number of sources which are well known and readily available to those skilled in the art. For example, *Remington's Pharmaceutical Sciences* (Martin E W [1995] Easton Pennsylavania, Mack Publishing Company, $19^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and non-aqueous sterile suspensions which may include suspending agents and thickening agents. The formulations maybe presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Therapeutically effective and optimal dosage ranges for the Aβ peptides can be determined using methods known in the art. Guidance as to appropriate dosages to achieve an anti-angiogenesis and/or anti-tumor effect is provided from the exemplified assays disclosed herein. For example, in the MATRIGEL plug model of angiogenesis (FIGS. 19A-19I), inhibition of angiogenesis was observed with 2 μM of Aβ peptide. In the tumor models (FIGS. 15A-15H and FIGS. 16A-16D) complete inhibition of tumor growth was observed with 10 μM of Aβ peptide. The minimal amounts of Aβ peptide to achieve a therapeutic effect can likewise be determined. In one embodiment, the Aβ peptide is administered in an equivalent amount to be within the μM dose range. In another embodiment, an amount equivalent to about 1 μM to about 100 μM Aβ peptide is administered. In another embodiment, an amount equivalent to about 2 μM to about 10 μM Aβ peptide is administered.

The subject invention also pertains to diagnostic and/or screening methods and kits to screen for compounds that are potentially therapeutic in treatment of Alzheimer's disease by interfering with the anti-angiogenic effect of the Aβ peptide.

In one aspect, the subject invention includes a method for identifying compounds that interfere with Aβ-induced angiogenesis inhibition, wherein the method includes the steps of (a) contacting a first biological sample capable of undergoing angiogenesis with a test compound, a biologically active amount of an Aβ peptide, and an angiogenic agent; and (b) determining the extent of angiogenesis that occurs in the first biological sample. Optionally, the method can include the steps of: (c) separately contacting a second biological sample capable of undergoing angiogenesis with a biologically active amount of an Aβ peptide and an angiogenic agent; (d) determining the extent of angiogenesis that occurs in the second biological sample; and (e) comparing the extent of angiogenesis that occurs in the first biological sample with that which occurs in the second biological sample. In this way, steps (c)-(d) can be utilized as a control. Preferably, the same Aβ peptide is used in the first and second biological samples. For example, the Aβ peptide utilized in the methods and kits of the subject invention can have an amino acid sequence corresponding to SEQ ID NO. 1, SEQ ID NO. 2, SEQ ID NO. 3, SEQ ID NO. 7, SEQ ID NO. 8, SEQ ID NO. 9, SEQ ID NO. 10, or SEQ ID NO. 11, or a biologically active fragment or variant thereof.

Determining the extent of angiogenesis can be carried out using methods known in the art, such as those described herein, and can be done qualitatively or quantitatively. For example, molecular or cellular markers of cancer or tumor growth can be utilized. The extent of angiogenesis can also be determined by measuring the amount of endothelial cell proliferation or the extent of blood vessel growth within a biological sample.

The biological samples utilized in the methods and kits of the subject invention can include various biological fluids and tissues that can exhibit angiogenesis and/or tumor development. For example, the biological sample can be arterial tissue, corneal tissue, endothelial cells, umbilical cord tissue, chorionic allantoid membrane, and the like.

The angiogenic agent can be any molecule, compound, or cell that is capable of inducing angiogenesis in the biological sample. For example, the angiogenic agent can be a trophic factor, such as a neurotrophic factor. The angiogenic factor can be a cytokine or growth factor such as vascular endothelial growth factor, platelet-derived growth factor, and basic fibroblast growth factor. The diagnostic and/or screening methods of the subject invention can be carried out in vivo, such as in an animal model, or in vitro.

In another aspect, the subject invention includes a kit for identifying compounds that interfere with Aβ-induced angiogenesis inhibition. The kit can include a compartment containing at least one Aβ peptide and, optionally, a compartment containing an angiogenic agent. Furthermore, the kit can optionally include a compartment containing one or more biological samples.

In another aspect, the subject invention includes method for identifying compounds that interfere with Aβ-induced anti-tumor activity, including the steps of: (a) contacting a first tumor tissue with a test compound and a biologically active amount of an Aβ peptide; and (b) determining the extent of tumor growth that occurs in the tumor tissue. Optionally, the method can further include the steps of: (c) separately contacting a second tumor tissue with a biologically active amount of an Aβ peptide; (d) determining the extent of tumor growth that occurs in the second tumor tissue; and (e) comparing the extent of tumor growth that occurs in the first tumor tissue with that which occurs in the second tumor tissue. In this way, steps (c)-(d) can be utilized as a control. The extent of tumor growth can be determined quantitatively or qualitatively using methods known in the art, including methods described herein. For example, molecular or cellular markers of cancer or tumor growth can be utilized.

In another aspect, the subject invention includes a kit for identifying compounds that interfere with Aβ-induced anti-tumor activity. The kit can include a compartment containing at least one Aβ peptide and, optionally, a compartment containing at least one tumor tissue. Furthermore, the kit can optionally include a compartment containing one or more biological samples.

The test compounds that can be screened using the methods and kits of the subject invention can include any substance, agent, or molecule, including, for example, small molecules and living or dead cells.

As used herein, the term "biological activity" with respect to the Aβ peptides of the subject invention refers to inhibition of angiogenesis. Thus, cell-based assays can be utilized to determine whether an agent, such as a nucleotide or polypeptide, can be utilized to carry out the method of angiogenesis inhibition of the subject invention.

The term "means for modulating (enhancing or suppressing) Aβ peptide function" comprises genetic and non-genetic means for modulating Aβ peptide function. Among the genetic constructs modulating Aβ peptide function, are various "gene delivery vehicles" known to those of ordinary skill in the art, that facilitate delivery to a cell of, for example, a coding sequence for expression of a polypeptide, such as an Aβ peptide inhibitor, an anti-sense oligonucleotide, an RNA aptamer capable of inhibiting Aβ peptide function, or other genetic construct capable of inhibiting Aβ peptide function at the transcription, translation, or post-translation level. Methods of gene silencing and/or knock-down, as described herein, and as known to those of ordinary skill in the art, can be utilized to suppress Aβ peptide function, for example. For example, gene therapy comprising administration of a dominant negative Aβ peptide mutant can be utilized.

Among the non-genetic means for modulating (enhancing or suppressing) Aβ peptide function are pharmaceutical agents, or pharmaceutically acceptable salts thereof, which are preferably administered in a pharmaceutically acceptable carrier.

The term "patient", as used herein, refers to any vertebrate species. Preferably, the patient is of a mammalian species. Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales.

The terms "Aβ" and "Aβ peptide" are used herein interchangeably to refer to the Aβ gene, its polypeptide product, or a biologically active fragment or variant of the polypeptide product, and includes Aβ peptide homologs (such as mammalian orthologs) and isoforms, unless otherwise noted. As indicated above, "biological activity" in the context of the Aβ peptides refers to anti-angiogenesis activity, and hence, can include anti-cancer or anti-tumor activity.

The terms "comprising", "consisting of", and "consisting essentially of" are defined according to their standard meaning and may be substituted for one another throughout the instant application in order to attach the specific meaning associated with each term.

As used herein, the term "angiogenesis" is intended to refer to the fundamental process by which new blood vessels are formed and which is essential to a variety of normal body activities (such as reproduction, development, and wound repair). The process is believed to involve a complex interplay of molecules which both stimulate and inhibit the growth of endothelial cells, the primary cells of the capillary blood vessels. Under normal conditions, these molecules appear to maintain the microvasculature in a quiescent state (i.e., one of no capillary growth) for prolonged periods. When necessary, however (such as during wound repair), these cells can undergo rapid proliferation and turnover within a short period of time. Although angiogenesis is a highly regulated process under normal conditions, many conditions (characterized as "angiogenic diseases") are driven by persistent unregulated angiogenesis. Otherwise stated, unregulated angiogenesis may either cause a particular pathological condition directly or exacerbate an existing pathological condition. For example, ocular neovascularization has been implicated as the most common cause of blindness and dominates approximately twenty eye diseases. In certain existing conditions, such as arthritis, newly formed capillary blood vessels invade the joints and destroy cartilage. In diabetes, new capillaries formed in the retina invade the vitreous, bleed, and cause blindness. Growth and metastasis of tumors are also angiogensis-dependent (Folkman, J., *Cancer Research*, 46:467-473, 1986; Folkman, J., *Journal of the National Cancer Institute*, 82:4-6, 1989). It has been shown, for example, that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant site, such as liver, lung or bone (Weidner, N. et al., *The New England Journal of Medicine*, 324(1):1-8, 1991).

Materials and Methods

Angiogenesis Assay. Twenty four well tissue culture grade plates (Nalgen International, N.Y.) were covered with 250 µL of MATRIGEL (BECTON-DICKINSON, Bedford, Mass.) and allowed to gel for 30 min at 37° C., 5% $CO_2$. Artery cultures were realized as previously described (Kruger et al. (2000) *Biochem. Biophys. Res. Commun.* 268, 183-191) with minor modifications. Briefly, thoracic aortae were excised from 9 month-old Sprague Dawley rats and from 9 month-old transgenic APPsw and control mice. Middle cerebral arteries were obtained from one year-old cows (Holstein, post-mortem delay of 2 hours) and from 3 different human cases (age ranging from 69 to 81 years) following a post-mortem delay of 4 to 5 hours. After removing the fibroadipose tissue, arteries were sectioned into 1 mm long cross sections, rinsed 5 times with EGM-2 (CLONETICS CORP.), placed on the MATRIGEL coated wells; then covered with an additional 250 µL of MATRIGEL containing 0, 1 or 5 µM of freshly solubilized $Aβ_{1-40}$ ($H_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH) (SEQ ID NO. 3) (BIOSOURCE, CA), or 5 µM of scramble $Aβ_{1-40}$ peptide (Val-Ile-Gly-Lys-Tyr-His-Gly-Met-Ser-Asn-Leu-Val-Gly-Arg-Ser-Phe-Glu-Val-His-Gln-Gly-Lys-Gly-Ala-Glu-Val-Asp-Ala-His-Gly-Leu-Phe-Asp-Ile-Glu-Ala-Phe-Val-Asp-Val) (SEQ ID NO. 4) (QUALITY CONTROL BIOCHEMICALS INC., MA), or 20 µM of the selective cyclooxygenase-2 (COX-2) inhibitor NS-398 (CALBIOCHEM, CA). The rings were cultured for 24-h in 2 mL of EGM-2 medium. After the 24-h incubation, the medium was replaced with 2 mL of EBM (CLONETICS Corp.), supplemented with 2% fetal bovine serum and 1× penicillin-Streptomycin-Fungizone mixture (BIOWHITTAKER, Walkersville, Md.) containing the same concentration of $Aβ_{1-40}$ ($H_2$N-Asp-Ala-Glu-Phe-Arg-His-Asp-Ser-Gly-Tyr-Glu- Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH) (SEQ ID NO. 3), scramble $A\beta_{1-40}$ peptide (Val-Ile-Gly-Lys-Tyr-His-Gly-Met-Ser-Asn-Leu-Val-Gly-Arg-Ser-Phe-Glu-Val-His-Gln-Gly-Lys-Gly-Ala-Glu-Val-Asp-Ala-His-Gly-Leu-Phe-Asp-Ile-Glu-Ala-Phe-Val-Asp-Val) (SEQ ID NO. 4) or NS-398. Control experiments for the different angiogenesis models were performed to determine the optimum timeframe for image acquisition. For the rat aortic ring assay, pictures were taken at day five using a 2× objective; for the bovine assay, pictures were sequentially taken at day 6, day 7 and day 9; for the mouse assay pictures were taken at day 4, 5 and 6; for the human model of angiogenesis, rings were photographed at day 9.

Quantification of Ring Microvessel Outgrowths. Microvessel outgrowth area was quantified using the IMAGE PRO PLUS software (MEDIA CYBERNETIC, INC., MD). Briefly, ring cultures were photographed using a digital video camera linked to an OLYMPUS BX60 microscope. The outgrowth area was selectively measured and detected with the Image Pro Plus software by using a strategy of microvessel outgrowths detection based on difference in color intensities between the outgrowths, the MATRIGEL and the artery ring. The artery rings were manually selected and excluded from the area measurement and a threshold was adjusted in order to selectively measure the area occupied by the microvessel outgrowths. Results were expressed in mean square pixels per ring. Statistical analysis was performed using ANOVA and post-hoc comparisons using Scheffe's or Bonferroni method, or t test for independent samples where appropriate using SPSS for WINDOWS release 10.1.

Isolation and Culture of Endothelial Cells From the New Microvessel Outgrowths. Pieces of MATRIGEL containing microvessel outgrowths from cow and human middle cerebral arteries were dissected out under an inverted microscope and minced several time through a sterile pipette tip in EBM medium. MATRIGEL fragments were then plated on glass coverslips, and incubated in EBM medium supplemented with 2% fetal bovine serum and 1× penicillin-Streptomycin-Fungizone mixture at 37° C., 5% $CO_2$ with the medium changed every three days. After 5 to 6 days in culture, cells were subjected to immunostaining with an antibody against factor VIII and an antibody against α-smooth muscle actin.

Factor VIII and α-Smooth Muscle Actin Immunostaining. Cells were washed in 0.1 M PBS (pH 7.4) and fixed with 4% paraformaldehyde for 20 min. After three washes with 0.1 M PBS (pH 7.4), cells were processed with the pre-blocking step, prior to an indirect double immunofluorescence staining as previously described (Dorovini-Zis et al. (1991) *Laboratory Investigation* 64, 425-436). Rabbit anti human Von Willebrand Factor (Factor VIII) antibody was used as an endothelial cells marker (DAKO, CA, diluted 1:50), mouse anti human α-Smooth Muscle Actin monoclonal antibody was used as a marker of smooth muscle cells (Clone 1A4, DAKO, CA, diluted 1:50). A FITC-conjugated secondary antibody (Goat anti rabbit IgG, Chemicon, CA, diluted 1:50) and TRITC-conjugated secondary antibody (Rabbit anti mouse IgG, DAKO, CA, diluted 1:50) were used to detect Factor VIII and α-smooth muscle actin antibody staining, respectively. Additionally, 0.1 M PBS was used instead of the primary and/or secondary antibodies as a negative control to assess the specificity of the staining procedure. Primary rat brain smooth muscle cell cultures were established as previously described (Diglio et al (1993) *Tissue Cell.* 25,833-846), used as a positive control for α-smooth muscle staining and as a negative control for factor VIII immunostaining. After the double-immunostaining procedure, cells were visualized under a fluorescence microscope (Olympus BX-60) using a dual FITC/TRITC filter.

Aβ and VEGF ELISAs. $A\beta_{1-40}$ levels were determined by ELISA (Biosource) according to the recommendations of the manufacturer using the cell culture medium surrounding the explants of aortic rings from control and Tg APPsw mice following a 24 hour incubation at 37° C. Results are expressed in pg/ml of $A\beta_{1-40}$ produced per aortic ring and per 24 hours. VEGF was measured from the cell culture medium of confluent primary cultures of control and Tg APPsw aortic endothelial cells using an ELISA kit (R&D). Results were expressed in pg of VEGF produced per 24 hours and per mg of protein.

Tube Formation by Human MCA Endothelial Cells. Two hundred µl of MATRIGEL were placed into each well of a 24-well culture plate at 4° C. and allowed to polymerize by incubation at 37° C. Human MCA endothelial cells ($5 \times 10^4$) were seeded on the MATRIGEL in 1 ml of EBM medium containing 4% fetal calf serum. The cells were incubated at 37° C. for 20 hours in a humidified 5% $CO_2$ atmosphere in the presence or absence of Aβ. Cells were treated with 500 nM or 5 µM of freshly solubilized $A\beta_{1-40}$ ($H_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH) (SEQ ID NO. 3), $A\beta_{1-42}$ ($H_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH) (SEQ ID NO. 2). Similar treatments of the cells were also performed with aggregated preparations of Aβ that were obtained after incubating Aβ for a week at 37° C. in PBS at a concentration of 500 µM. The experiments were performed in quadruplicate for each treatment conditions were performed. For each culture, two to three randomly chosen fields were photographed using a 4× objective. The total length of tube structures in each photograph was measured using the Image Pro Plus software.

Endothelial Cell Migration Assay. Migration of human brain adult endothelial cells was evaluated using a modified Boyden chamber assay (BD BioCoat MATRIGEL Invasion Chamber), as described (Soker et al. 1998; Nakamura et al. 1997). The cells were plated at $4.10^4$/ml onto an 8 µm pore size membrane coated with a thin layer of MATRIGEL basement membrane matrix. Freshly solubilized Aβ (1 µM and 5 µM) was added to the medium in the outer cup and the cells were cultured for 20 hours. Non-invading cells were removed from the upper surface by using a cotton swab. Membrane inserts were then fixed with 4% paraformaldehyde and stained with the DEAD-RED dye (MOLECULAR PROBE). Cells were observed using a fluorescent microscope. The number of cells, which migrated to the undersurface of the filter, was quantified by counting the cells in randomly selected 3 microscopic fields (10×). Experiments were done in triplicate.

Measurement of Microvessel Density in the Cortex and Hippocampus of Control and Tg APPsw mice. Mice were deeply anesthetized with isofluorane and perfused transcardially with 10 ml of 0.1 M PBS, then with 10 ml of 4% paraformaldehyde in 0.1 M PBS and finally with 10 ml of India ink. The brains were removed from the skull and immersed in 20% sucrose containing 2% paraformaldehyde for 18 hours at 4° C. Brains were embedded in OCT compound and freeze with dry ice-hexane. Brains were cut into serial 18 µm thick coronal sections on a freezing microtome. Sections were mounted on silinized coated slides and covered with a coverslip. Only the sections containing the hippocampus were analyzed. The area covering the motor cortex and the entire hippocampus were photographed using a 10×objective and microvessel density determined using the Image Pro Plus software (Media cybernetic). The projected areas of capillaries ($ÓA'_I$) were measured by using a histogram-based threshold filling all the capillaries. Capillary surface area per unit of volume (Sv) was calculated as follow for the hippocampus and cortex using a 10× magnification: Sv=4ÓA'/(section thickness*area) as previously described (Pawlik et al. Brain Res. 208, 35-58 (1981); Boero et al. J. Appl. Physiol. 86, 1211-9 (1999)). Pixels were converted to μm according to digitized calibrated scales in function of the magnification used. Each value for an individual mouse was determined from at least 10 serial sections. All values were reported as means from 3 control and 3 Tg APPsw mice aged of 16 months. Randomly selected sections from Tg APPsw mice were also stained with congo red as previously described (Paris et al., Neurobiology of Aging, 21:183-197, 2000) and areas containing senile plaques like formations were photographed.

Subcutaneous Implantation of B16 Melanoma Cells. C57B16/J mice were purchased from Jackson laboratories at 8 weeks of age. The B16 F1 murine melanoma cell line was purchased from ATCC. Cells were grown in DMEM medium supplemented with 10% fetal calf serum and 1× mixture of antibiotics-fungicide (BIOWHITEKER). After reaching confluence, cells were trypsinized and resuspended at a density of $6.10_4$ cells/100 μl in DMEM culture medium (control) or in DMEM medium containing 10 μM of freshly dissolved $Aβ_{1-40}$ ($H_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH) (SEQ ID NO. 3). 100 μl of cell suspension were injected subcutaneously in mice. Fourteen days after the implantation of the cells, mice were euthanized and the tumors dissected and weighted.

Capillary Network Formation with Dutch $Aβ_{1-40}$. Human brain endothelial cells ($5×10^4$) were seeded on the top of a MATRIGEL layer in 1 ml of EBM (CAMBREX BIO SCIENCE, MD) containing 4% fetal calf serum. The cells were incubated in the presence or absence of different concentrations of soluble $Aβ_{1-40}$, $Aβ_{1-42}$ or soluble Dutch $Aβ_{1-40}$ ($H_2$N-Asp-Ala-Glu-Phe-Arg-His-Asp-Ser-Gly-Tyr-Glu-Val-His-His-Gln-Lys-Leu-Val-Phe-Phe-Ala-Gln-Asp-Val-Gly-Ser-Asn-Lys-Gly-Ala-Ile-Ile-Gly-Leu-Met-Val-Gly-Gly-Val-Val-Ile-Ala-Thr-OH) (SEQ ID NO. 8) at purity greater than 95% (BIOSOURCE, CA) as indicated in the figure legends. The experiments were performed in quadruplicate and at least 2 to 3 randomly chosen fields were photographed using a 4× objective. Capillary length was measured using the IMAGE PRO PLUS software (MEDIA CYBERNETIC, INC., MD).

Nude mouse tumor xenograft model. A-549 (human lung adenocarcinoma) and U87-MG (human glioblastoma) cells were harvested, resuspended in PBS and implanted subcutaneously into the right and left flank ($10×10^6$ cells/flank) of 8-week-old female nude mice (HARLAN, Indianapolis, Ind.). When tumors reached about 150 $mm^3$, animals were dosed intratumorally with either 50 μl dd$H_2$O vehicle (control group), $Aβ_{1-40}$ (50 mg/kg/day/tumor) or scrambled Aβ (50 mg/kg/day/tumor) dissolved in dd$H_2$O. The tumor volumes were determined by measuring length (l) and width (w) and calculating volume ($V=lw^2/2$). On the termination day of each in vivo antitumor study, tumors were extracted and fixed in 10% neutral buffered formalin for 6 h. Formalin-fixed paraffin sections were cut at 3 microns and dried overnight at room temperature. Sections were immunostained with rat anti-mouse CD31 (PHARMINGEN, San Diego, Calif.) using the avidin peroxidase complex technique as previously described (Blaskovich M. A., et al. Nat. Biotechnol. 18, 1065-1070 (2000)). Briefly, sections were digested with protease XXIV (1 mg/ml in PBS, pH 7.6) for 7 minutes. Endogenous peroxidase was blocked with 3% hydrogen peroxide and non-specific background staining reduced by a 10 min incubation with normal rabbit serum. Sections were incubated for 30 min with rat anti-mouse CD31 at 1:50, for 15 min with biotinylated anti-rat IgG and for 15 min with ABC complex (VECTOR KIT, Burlingame, Calif). NOVARED was used as the chromogen. Slides were counterstained with modified Mayer's hematoxylin using standard histological techniques. For microvessel counting, the five areas of highest tumor neovascularization were microscopically selected using a low-power view. After the areas of highest neovascularization had been identified, individual microvessels were counted on a 400×(40× objective lens and 10× ocular lens) field. Brown-staining endothelial cells or endothelial cell clusters were considered as a single, countable microvessel as previously described (Weidner N. et al. N. Engl. J. Med. 324, 1-8 (1991)). Data from at least forty 400× fields of each tumor type are reported by mean values±SE. Results are expressed as the % of microvessel count standardized against the microvessel count in the control tumors (vehicle only).

EXAMPLE 1

Modulation of Endothelial Cells Migration by Aβ

The construction of a vascular network requires different sequential steps, including the release of proteases from "activated" endothelial cells with subsequent degradation of the basement membrane surrounding the existing vessel, migration of endothelial cells into the interstitial space, endothelial cell proliferation, and differentiation into mature blood vessels. The migration of human brain endothelial cells through a filter coated with a reconstituted basement membrane (MATRIGEL) was investigated. Data revealed that 1 μM of Aβ stimulated endothelial cell migration while at 5 μM Aβ significantly suppressed endothelial cells migration compared to untreated cells, as shown in FIGS. 1A-1D.

EXAMPLE 2

Effect of Aβ on Capillary Network Formation

Although endothelial cells continue to proliferate and form a cobblestone monolayer when plated on untreated tissue culture dishes, culturing on dishes coated with reconstituted basement membrane induces endothelial cells to become quiescent and adopt a three-dimensional capillary-like morphology. Therefore, the effect of Aβ on the capillary-like network formation on MATRIGEL by endothelial cells isolated from human middle cerebral artery was assessed. Capillary morphogenesis appears to be enhanced by a low dose of freshly solubilized $Aβ_{1-40}$ or $Aβ_{1-42}$ (500 nM) whereas a higher dose of these peptides (5 μM) significantly reduced the formation of capillary-like networks, as shown in FIGS. 2A-2G. Under soluble or aggregated forms $Aβ_{1-40}$ displays similar properties however low doses of aggregated $Aβ_{1-42}$ (500 nM) appears to loose their pro-angiogenic effect and 5 μM of aggregated $Aβ_{1-42}$ displays even more potent anti-angiogenic activity than freshly solubilized $Aβ_{1-42}$ (FIG. 2). $Aβ_{1-42}$ is known to be more amyloidogenic than $Aβ_{1-40}$ and displays more potent anti-angiogenic activity than $Aβ_{1-40}$ suggesting that the antiangiogenic activity of these peptides could be related to their β-sheet content. The potential toxicity of Aβ was investigated in this assay and it was observed that under these culture conditions no apoptosis (as measured by ELISA determining the quantity of cytoplasmic oligonucleosomes) or necrosis (estimated by the release of LDH in the culture medium) of endothelial cells was induced by either soluble or aggregated Aβ (data not shown). These data indicate that basement membrane-induced capillary morphogenesis of human brain endothelial cells is dose dependently influenced by Aβ species.

EXAMPLE 3

Effect of Aβ on Angiogenesis Using the ex vivo Rat Aortic Ring Assay Model

Formation of new microvessels in the rat aortae model of angiogenesis is a self-limited process mediated by autocrine/paracrine mechanism triggered by the injury of the dissection procedure (Nicosia et al. (1997) *Amer. J. Path.* 151, 1379-1385). In this model, the rat aortic endothelium exposed to a three-dimensional matrix switches to a microvascular phenotype generating branching networks of microvessels (Kruger et al. (2000) *Biochem. Biophys. Res. Commun.* 268, 183-191; Nicosia et al. (1992) *Atherosclerosis* 95, 191-199). The effect of $A\beta_{1-40}$ on the formation of new microvessels was assessed in this model. $A\beta_{1-40}$ was reconstituted in endothelial cell basal media and incubated on rat aortic rings at different concentrations for 5 days. Interestingly, a low dose of $A\beta_{1-40}$ (1 μM) stimulated microvessel outgrowths; whereas a 5 μM dose of $A\beta_{1-40}$ inhibited the formation of cellular outgrowths from the aortic rings, as shown in FIGS. 3A-3D. Quantitative image analysis confirmed the dose-dependent activity of $A\beta_{1-40}$ on microvessel outgrowths from rat aortic rings, as shown in FIG. 4. NS-398, a selective cyclooxygenase-2 (COX-2) inhibitor known to inhibit the angiogenic process (Jones et al. (1999) *Nat. Med* 5, 1418-1423) was used as a positive control in this assay and effectively inhibited outgrowths at 20 μM (FIGS. 3A-3D and FIG. 4). Interestingly, the stimulation of microvessel outgrowths by 1 μM $A\beta_{1-40}$ was also inhibited by NS-398 suggesting that COX-2 activity is required to mediate the pro-angiogenic effect of low doses of Aβ in the rat aortae model.

EXAMPLE 4

Antiangiogenic Activity of $A\beta_{1-40}$ on Cow and Human Middle Cerebral Arteries Having shown that $A\beta_{1-40}$ can modulate the angiogenesis process in peripheral vessels, the effect of Aβ on cerebrovessels was next examined. First, a bovine model of angiogenesis (derived from the rat aortae model) was investigated utilizing rings of middle cerebral artery instead of aortic rings. Sections of cow middle cerebral arteries are able to form microvessel outgrowths in MATRIGEL that gradually increased in size from day 6 to 9 (as shown in FIGS. 5A-5I). It was observed that $A\beta_{1-40}$ at 1 μM and 5 μM is able to significantly inhibit the formation of outgrowths from cow middle cerebral arteries during this period of time (FIGS. 5A-5I and FIG. 6). Again, COX-2 inhibition by NS-398 resulted in a partial inhibition of microvessel outgrowths confirming that eicosanoids derived from COX-2, like in the rat aortae assay, also play a critical role in middle cerebral artery angiogenesis (data not shown). To confirm the outgrowths from bovine middle cerebral arteries were endothelial cells, the tubelike/cordlike structures were isolated from MATRIGEL and these outgrowths were maintained in EBM medium. Under this condition, the tubelike structures progressively disappeared and were replaced by adherent and proliferating cells forming a monolayer within 5-6 days in culture. Factor VIII-related antigen (Von Willebrand factor) immunostaining (Kruger et al. (2000) *Biochem. Biophys. Res. Commun.* 268, 183-191; Diglio et al. (1982) *Lab. Invest.* 46, 554-563) revealed that these cells were endothelial cells (FIGS. 10A-10F) and suggested that the outgrowths from middle cerebral arteries were proliferating endothelial cells.

Figure 8:
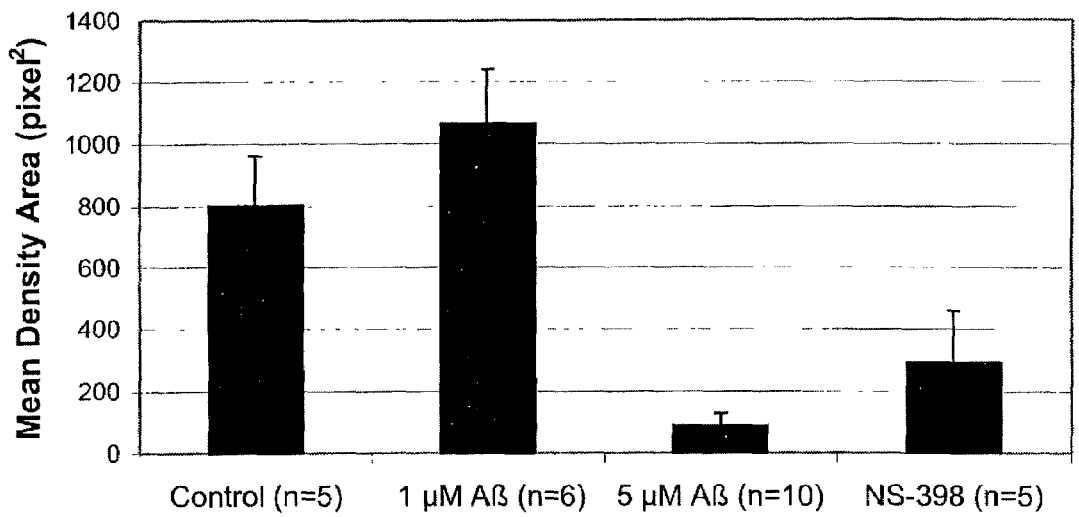
FIG. 8 shows the quantification of microvessel outgrowths in response to $A\beta_{1-40}$ and NS-398 treatment on human middle cerebral artery rings (isolated from a 69 year-old patient after a 4 hour post-mortem delay). Image analysis of human middle cerebral artery rings shows the anti-angiogenic effect of 5 µM $A\beta_{1-40}$ and of NS-398. ANOVA revealed significant main effects of $A\beta$ dose (P<0.001) and NS-398 (P<0.01). Post-hoc comparison showed a significant difference between control and 5 µM $A\beta_{1-40}$ (P<0.005) and between control and NS-398 (P<0.05), but not between control and 1 µM $A\beta_{1-40}$ (P=0.179).
Figure 9A:
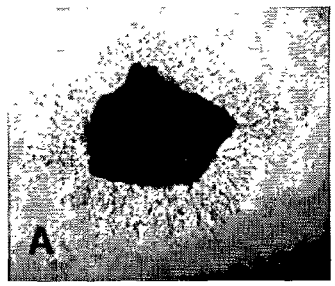
FIGS. 9A-9D show the absence of pro-angiogenic activity of 1 µM scramble $A\beta_{1-40}$ on human middle cerebral artery rings (isolated from an 81 year-old patient after a 5 hour post-mortem delay.
Figure 9B:
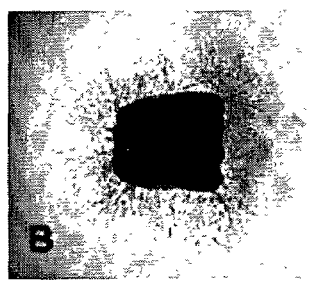
Figure 9C:
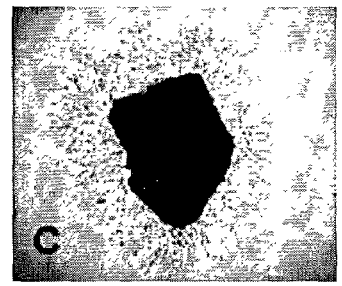
Figure 9D:
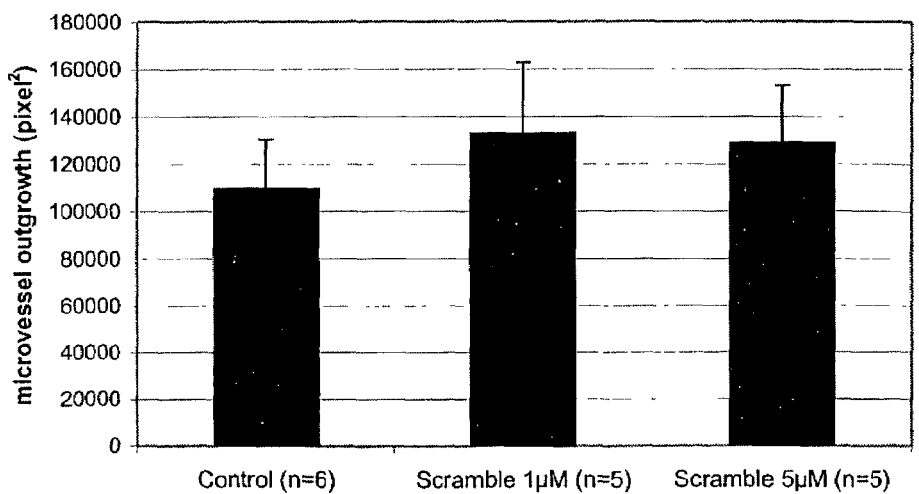
Figure 10A:
FIGS. 10A-10F show that microvessel outgrowths of bovine and human middle cerebral arteries are essentially constituted of endothelial cells. Cells isolated from microvessel outgrowths were immunostained for both Factor VIII (FITC) and α-smooth muscle actin (TRITC) and were visualized under a fluorescence microscope using a dual FITC/TRITC filter. Cells isolated from microvessel outgrowths of bovine middle cerebral artery (FIG. 10A) and from microvessel outgrowths of human middle cerebral artery (FIG. 10B) demonstrated immunoreactivity for factor VIII but not for α-smooth muscle actin.
Figure 10B:
Figure 10C:
Figure 10D:
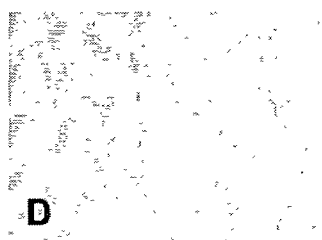
Figure 10E:
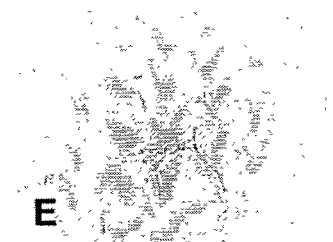
Figure 10F:
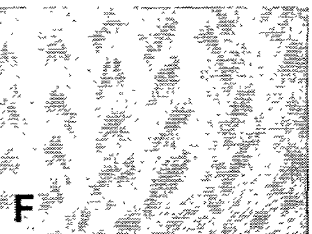
Figure 11A:
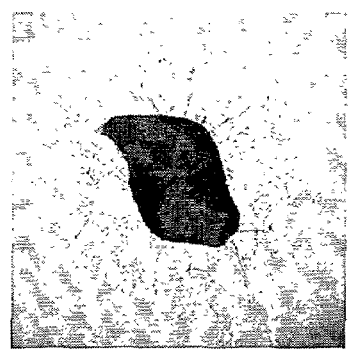
FIGS. 11A-11F show differential angiogenesis of control and Tg APPsw mice aortic rings.
Figure 11B:
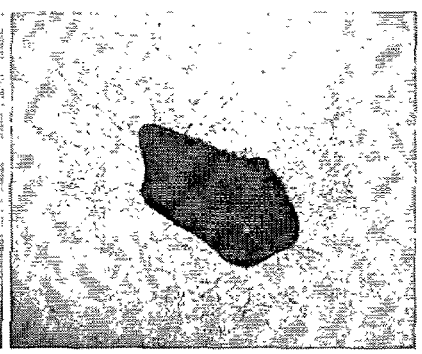
Figure 11C:
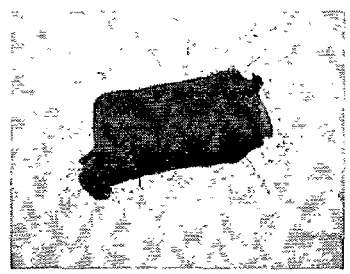
Figure 11D:
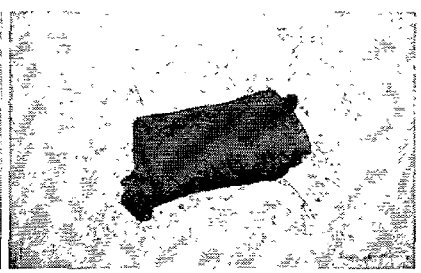
Figure 11E:
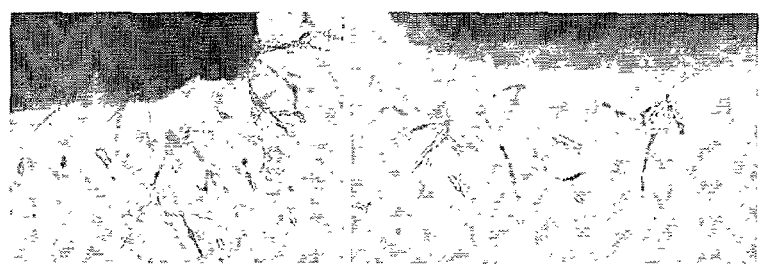
Figure 11F:
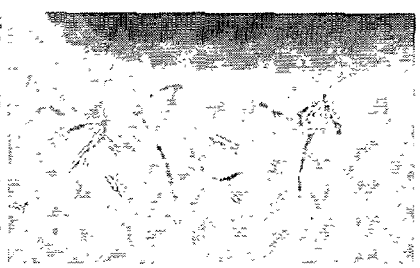
Figure 12:
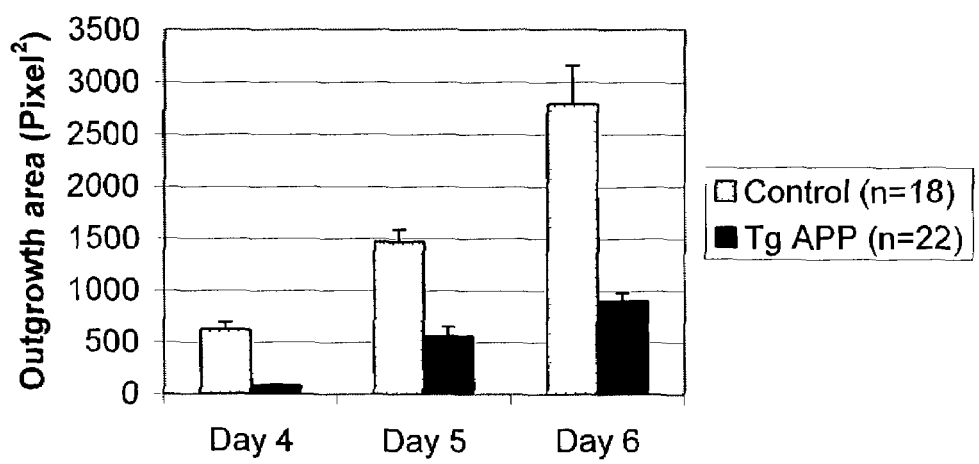
FIG. 12 shows the quantification of microvessel outgrowths from control and Tg APPsw mice aortic rings. Image analysis shows that microvessel outgrowths are significantly reduced in aortic rings from Tg APPsw compared to control mice. Error bars represent standard error and the number in parenthesis represents the number of aortic rings analyzed. ANOVA revealed significant main effects of transgenicity (P<0.001) and time (P<0.001) as well as an interactive term between them (P<0.001). Post-hoc testing showed significant differences between control and Tg APPsw (P<0.03) at day 5, control and Tg APPsw (P<0.001) at day 6, and between control at day 5 and control at day 6 (P<0.02).
Figures 13A, 13B:
FIGS. 13A-13E show the capillary densities in the brain of control and Tg APPsw mice. Representative sections showing capillaries distribution in the motor cortex of a control mouse (FIG. 13A) and a transgenic APPsw animal (FIG. 13B). Congo red staining. shows the presence of amyloid deposits in the cortex (FIG. 13C) and the hippocampus of Tg APPsw mice.
Figures 13C, 13D:
Figure 13E:
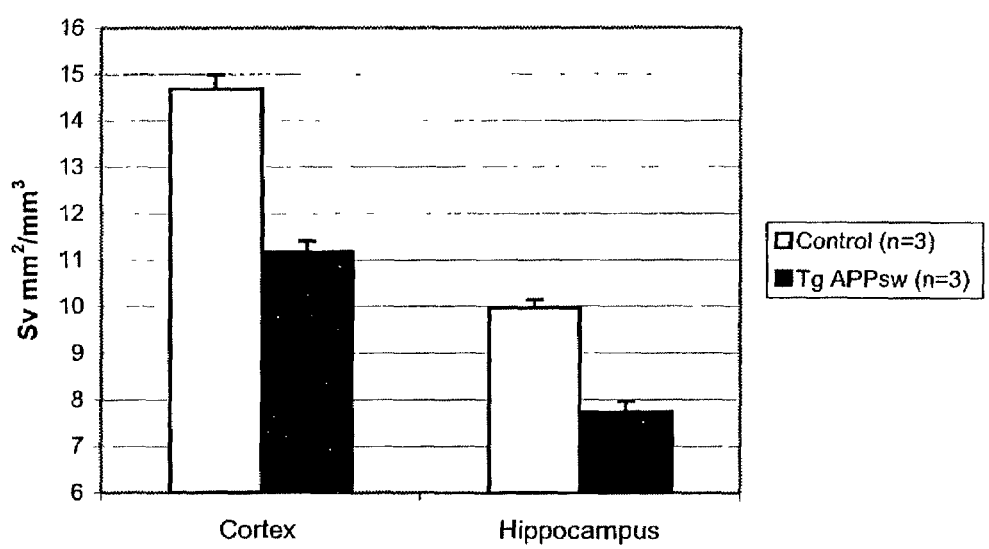

Next, a human model of the middle cerebral artery ring assay was examined to compare against the bovine system, incubating human middle cerebral artery rings for 9 days with different doses of Aβ. Five μM of $A\beta_{1-40}$ appeared to inhibit the microvessel outgrowths from human middle cerebral arteries (FIGS. 7A-7F and FIG. 8) showing that the antiangiogenic effect of Aβ is not species specific. One μM of $A\beta_{1-40}$ did not significantly stimulate microvessel outgrowths in the human middle cerebral artery model of angiogenesis contrarily to its effect on rat aortae (FIGS. 7A-7F and FIG. 8). It has to be point out that human middle cerebral arteries were collected from elderly patients and that the angiogenic potential is known to be reduced with aging. To assess the specificity of $A\beta_{1-40}$ effect on angiogenesis, the impact of a scramble $A\beta_{1-40}$ peptide (having the same amino acids as $A\beta_{1-40}$ peptide, but in random order) on angiogenesis was tested. Data showed that this scramble peptide is unable to affect the formation of outgrowths from human middle cerebral artery rings (FIGS. 9A-9D). In this human model of angiogenesis, inhibition of COX-2 by NS-398 also partially inhibited the microvessel outgrowths (FIG. 8). It was also confirmed in this system that the outgrowths were essentially composed of endothelial cells (FIGS. 10A-10F).

EXAMPLE 5

Angiogenesis in Aortic Rings From Control and Transgenic APPsw Mice

Having shown that synthetic Aβ can affect the angiogenic process in peripheral and cerebral arteries, the next objective was to determine whether the formation of microvessel outgrowths in aortic rings from transgenic mice overexpressing Aβ peptides would be altered. The APP transgene appears to be overexpressed in transgenic aortae leading to a significant increase in Aβ production (control aortae: $A\beta_{1-40}$ level undetectable; transgenic APPsw aortae: 51.6±6.6 pg of $A\beta_{1-40}$ were secreted following 18 hours of incubation in MATRIGEL). Data show (FIGS. 11A-11F and FIG. 12) that angiogenesis is reduced in Tg APPsw aortic rings compared to control aortae suggesting that endogenous overproduction of Aβ by cells of the vasculature can alter the angiogenic process. Primary cultures of endothelial cells from Tg APPsw and control aortae were established, and the production of vascular endothelial growth factor (VEGF) measured. Transgenic APPsw endothelial cells produce significantly less VEGF than endothelial cells from control animals (control endothelial cells: 43.2±0.86 pg VEGF/mg of protein/24 hours vs Tg APPsw endothelial cells: 2.5±0.42 pg VEGF/mg of protein/24 hours, P<0.001 by t-test for independent samples)

suggesting that chronic Aβ overexpression can alter VEGF production possibly leading to alteration of the angiogenic process.

EXAMPLE 6

Brain Microvessel Densities in Tg APPsw and Control Mice

Microvessel densities in the brain of Tg APPsw and control mice were examined after perfusion with India ink. In control animals, microvessel densities appear higher in the cortex compared to the hippocampus and display some values similar to previously published reports (Pawlik et al. *Brain Res.* 208, 35-58 (1981); Boero et al. *J. Appl. Physiol.* 86, 1211-9 (1999)). In Tg APPsw mice, capillary densities were also found to be higher in the cortex compared to the hippocampus. Moreover, image analysis revealed that microvessel densities are significantly reduced in the motor cortex and the hippocampus of 16 month-old Tg APPsw mice compared to control littermates (FIGS. 13A-13E). These data suggest that Aβ overexpression in the brain can lead to a reduction in vascular density.

EXAMPLE 7

Effect of Aβ on the Growth of Subcutaneous B16F1 Tumors

Figure 14A:
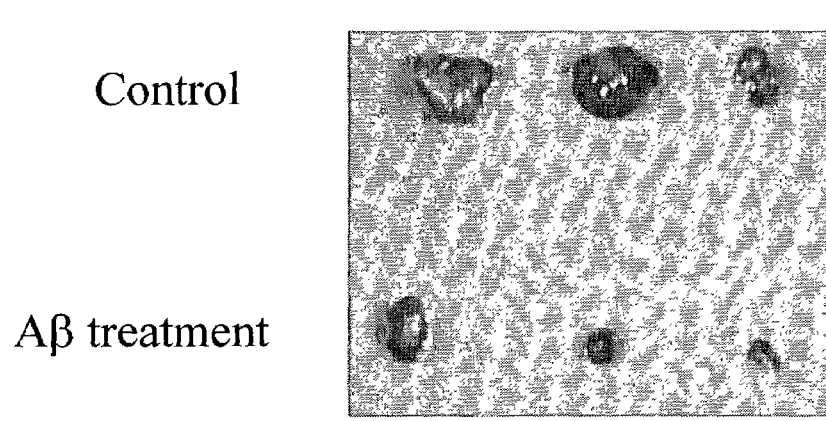
FIGS. 14A and 14B show the effect of $A\beta$ on tumor growth, as represented in a photograph of tumors excised from control mice and mice treated with $A\beta$. Mice were killed 14 days after implantation of tumor cells. At time of death, tumors were excised and weighed. Data shown are means±SEM for n=3 in each group.
Figure 14B:
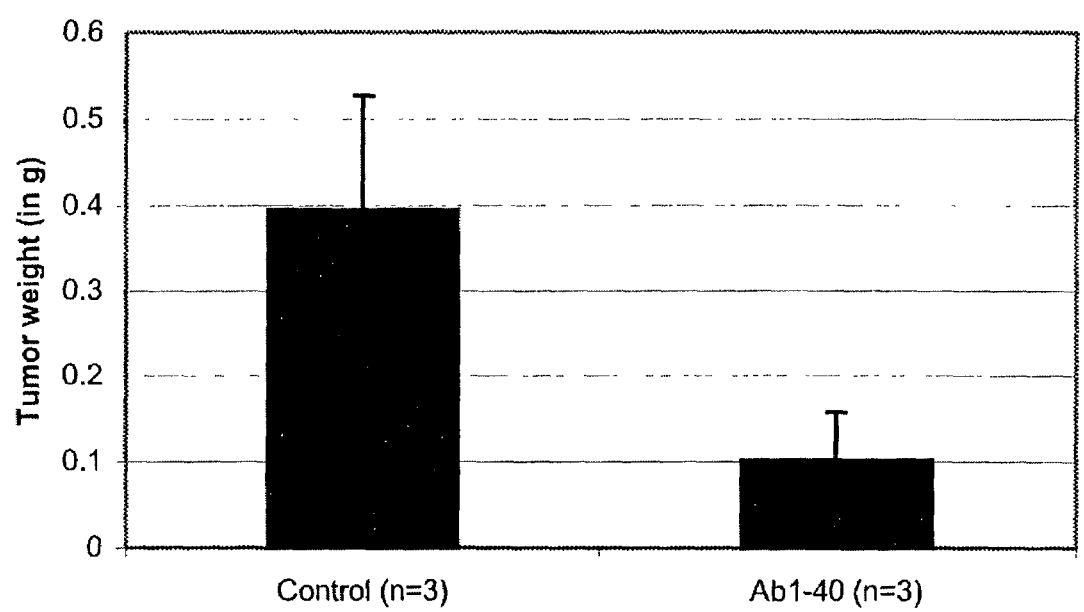

Since tumor growth is dependent on formation of new blood vessels for its supply of oxygen and nutrients (Fokman, J., *Ann. N.Y. Acad. Sci.,* 401:212-227, 1982), the effect of Aβ on tumor growth was assessed. Experimental tumors were induced by injecting B16F1 melanoma cells subcutaneously to C57B16/J mice. Fourteen days after the implantation, tumors were removed and weighed. Data revealed that Aβ can significantly reduce the development of tumors in mice (FIGS. 14A and 14B).

EXAMPLE 8

Figure 15A:
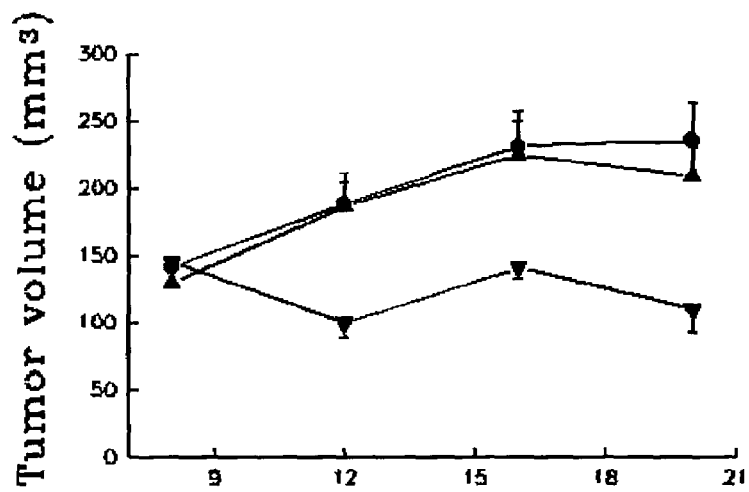
FIGS. 15A-15H shows the effect of $A\beta_{1-40}$ on human lung adenocarcinoma xenografts in nude mice. As shown by the graph in FIG. 15A, $A\beta_{1-40}$ suppresses human lung (A-549) tumor growth in nude mice. A-549 cells were implanted subcutaneously in nude mice and tumor volumes were measured over time. Bars represent standard error and data are representative of 6 tumors for scrambled $A\beta$ treatment and 8 tumors for both control and $A\beta$ treatment conditions: (●) control group (▲) scrambled $A\beta$ and (▼) $A\beta_{1-40}$ treated group. ANOVA revealed significant main effect for $A\beta_{1-40}$ treatment (P<0.001), time (P<0.001) as well as an interactive term between time and Aβ$_{1-40}$ treatment (P<0.003) but no significant main effect for scrambled Aβ (P=0.365). Post-hoc analysis showed significant differences between tumor volumes in the control group compared to the Aβ$_{1-40}$ treated group (P<0.001) but no difference between the control group and the scrambled Aβ group (P=0.735).
Figure 15B:
Figure 15C:
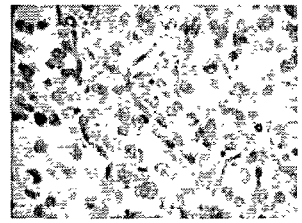
Figure 15D:
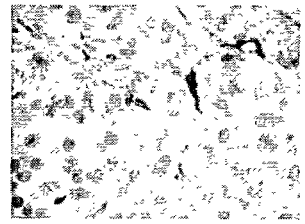
Figure 15E:
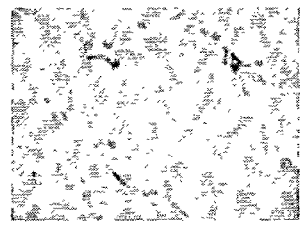
Figure 15F:
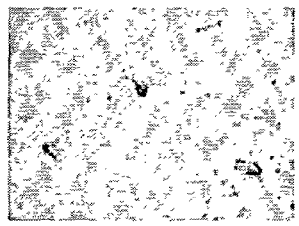
Figure 15G:
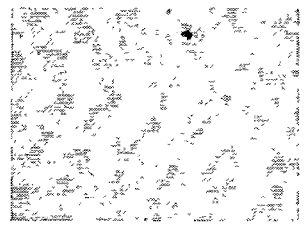
Figure 15H:
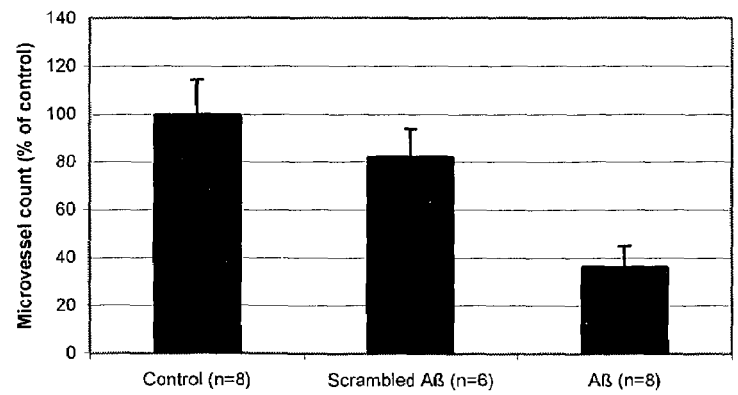
Figure 16A:
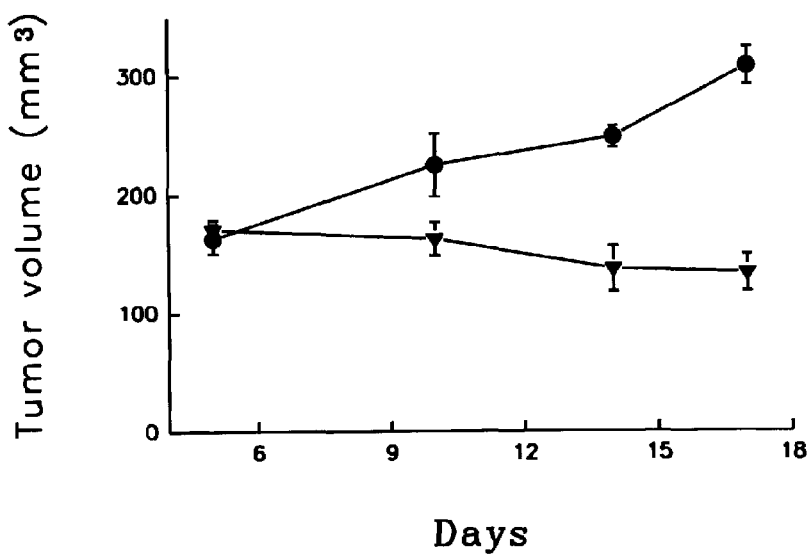
FIGS. 16A-16D show the effect of Aβ$_{1-40}$ on human glioblastoma xenografts in nude mice. U87-MG cells were implanted subcutaneously in nude mice and tumor volumes were measured over time. As shown by the graph in FIG. 16A, Aβ$_{1-40}$ suppresses human glioblastoma (U87-MG) tumor growth in nude mice. Bars represent standard error and data are representative of 8 tumors for each treatment condition: (●) control group and (▼) Aβ$_{1-40}$ treated group. ANOVA revealed significant main effect for Aβ$_{1-40}$ treatment (P<0.001), time (P<0.001) as well as an interactive term between time and Aβ$_{1-40}$ treatment (P<0.007).
Figures 16B, 16C:
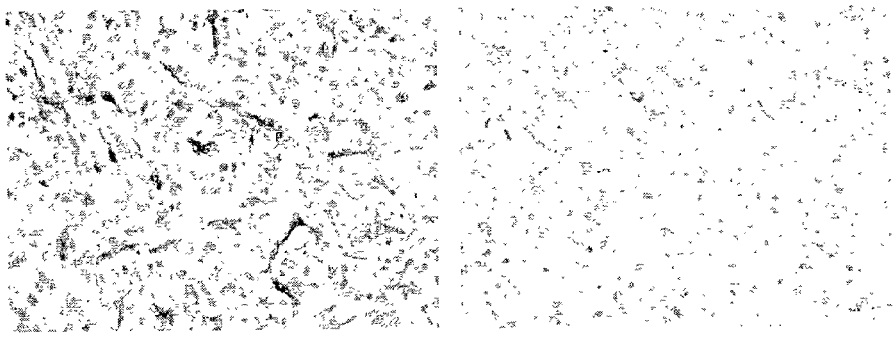
Figure 16D:
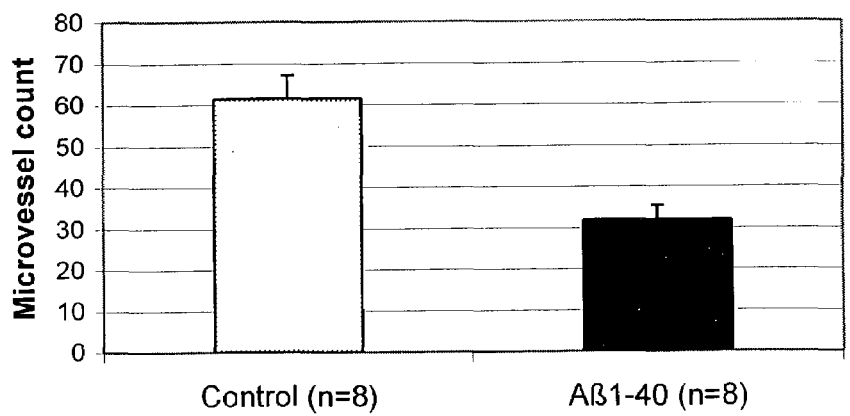
Figure 20A:
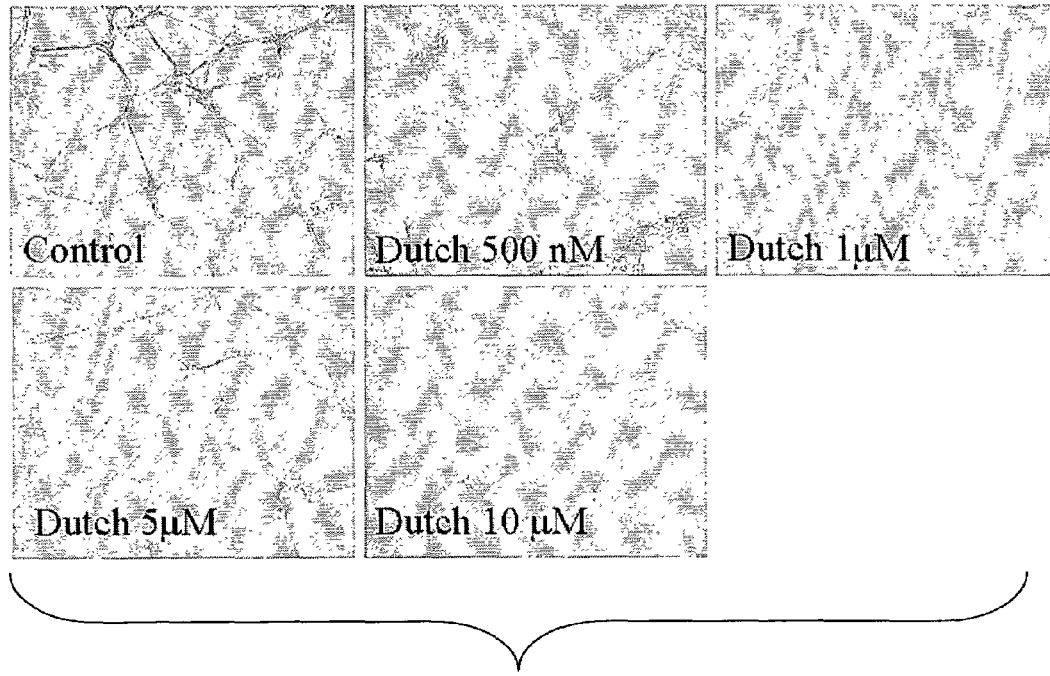
FIGS. 20A-20C show the effect of the Dutch Aβ$_{1-40}$ peptide (SEQ ID NO. 8) on angiogenesis.
Figure 20B:
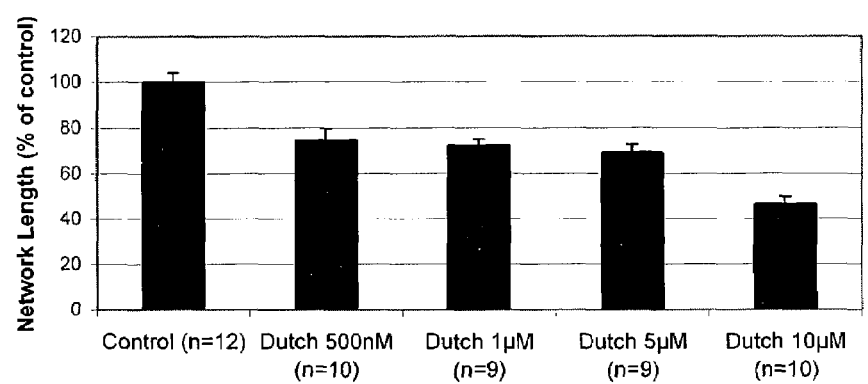
Figure 20C:
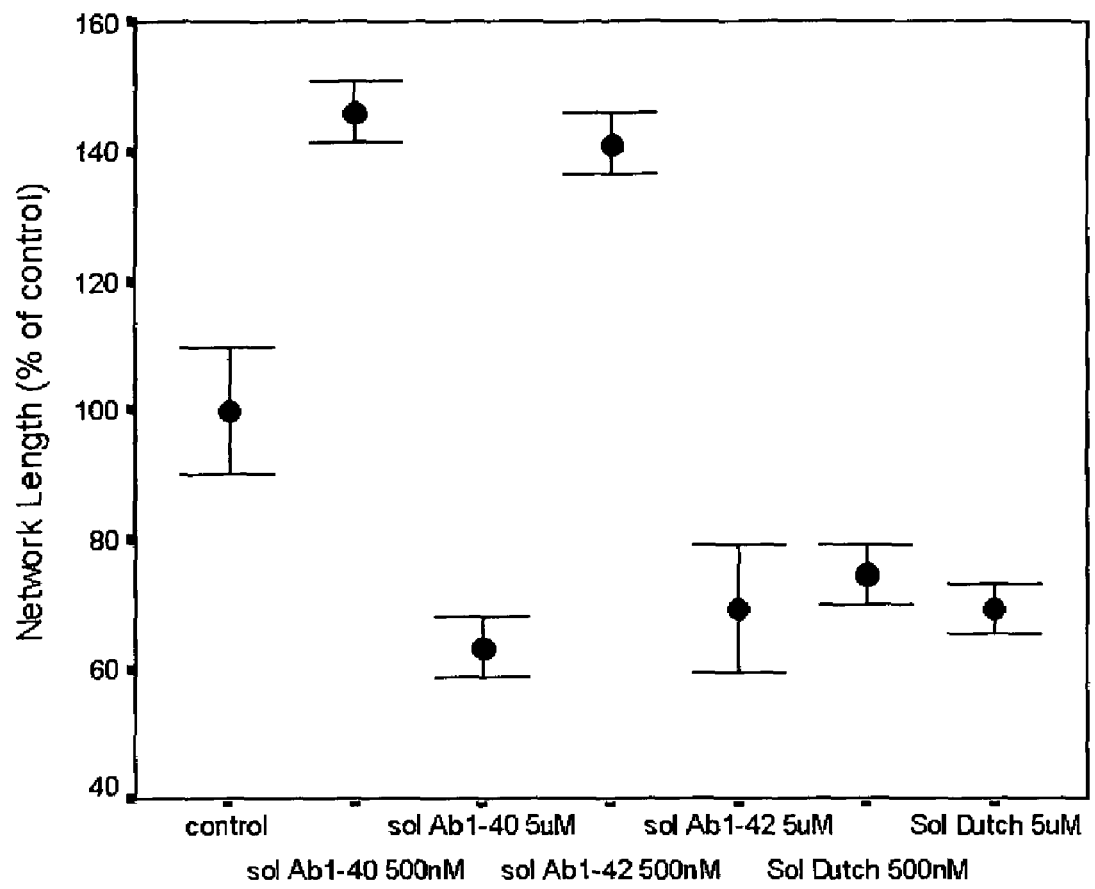

Effect of Aβ on the Growth and Vascularization of Human Glioblastoma (U87 MG) and Human Lung Adenocarcinoma (A-549) Xenografts in Nude Mice Tumor growth is generally dependent on formation of new blood vessels for its supply of oxygen and nutrients, this is particularly true for glioblastomas which are highly vascular malignant brain tumors (Brem S. et al. *J. Natl. Cancer. Inst.* 48, 347-356 (1972)). Therefore, the potential antitumoral activity of Aβ against human glioblastoma (U87 MG) and human lung adenocarcinoma (A-549) xenografts in nude mice was examined. Tumor volumes and microvessel densities of the tumors were determined. Interestingly, Aβ treatment resulted in a suppression of tumor growth for both tumor types (FIGS. 15A-15H and FIGS. 16A-16D) whereas the scrambled Aβ treatment did not affect the growth of human lung tumors showing the specificity of Aβ anti-tumoral effects. Tumor microvessel densities were evaluated by CD31 and factor VIII immunostaining in the lung tumor model and appeared to be reduced by approximately 60% following Aβ treatment whereas the Aβ scrambled treatment did not impede tumor vascularization (FIG. 15H). Microvessel densities were estimated by CD31 immunostaining in human glioblastoma xenografts and were reduced by approximately 50% following Aβ treatment (FIG. 16D) suggesting that Aβ suppresses tumor growth by inhibiting angiogenesis.

EXAMPLE 9

Effect of Aβ Peptide in the Chick Chorionic Allantoid Membrane (CAM) Model of Angiogensis $A\beta_{1-40}$ dose dependently inhibits angiogenesis in vivo in the CAM assay, as shown in FIGS. 17A-17H. A dose dependent inhibition of angiogenesis with $A\beta_{1-40}$ but not with scrambled Aβ, showing the specificity of the $A\beta_{1-40}$ anti-angiogenic effect in this in vivo assay.

EXAMPLE 10

Effect of Aβ Peptide in the Rat Corneal Model of Angiogenesis

The anti-angiogenic activity of Aβ was also confirmed in the avascular rat cornea assay, as shown in FIGS. 18A-18E. After 7 days, both $A\beta_{1-40}$ and $A\beta_{1-42}$ dose dependently inhibited neovascularization stimulated by bFGF (basic fibroblast growth factor) in the rat cornea whereas the scrambled Aβ peptide displayed no effect further confirming that Aβ peptides are antiangiogenic in vivo.

EXAMPLE 11

Effect of Aβ Peptide on bFGF-Induced Angiogenesis

The anti-angiogenic activity of $A\beta_{1-40}$ was also investigated in the in vivo MATRIGEL plug assay, as shown in FIGS. 19A-19H. MATRIGEL containing 100 ng/ml of bFGF was injected subcutaneously and mice were either treated for 6 days with an intraperitoneal injection of scrambled Aβ or human $A\beta_{1-40}$ (50 mg/Kg of body weight/day). Histologic sections of the MATRIGEL plugs indicated a significant inhibition of the angiogenic response in the $A\beta_{1-40}$ treated group compared to the group of animals treated with scrambled Aβ. In particular, endothelial cell invasion and vessel formations were inhibited as a consequence of the $A\beta_{1-40}$ treatment.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A method of inhibiting angiogenesis for the treatment of cancer in a patient in need thereof, said method comprising: administering an amount of an Aβ peptide sufficient to inhibit angiogenesis in said cancerous tissue to the patient, wherein the Aβ peptide consists of the amino acid sequence selected from the group consisting of SEQ ID NO. 1, SEQ ID NO. 2, SEQ ID NO. 3, SEQ ID NO. 7, SEQ ID NO. 8, SEQ ID NO. 9, SEQ ID NO. 10, and SEQ ID NO. 11.

2. The method according to claim 1, wherein the Aβ peptide consists of the amino acid sequence of SEQ ID NO. 1.

3. The method according to claim 1, wherein the Aβ peptide consists of amino acid sequence of SEQ ID NO. 8.

4. The method according to claim 1, wherein the Aβ peptide is administered to the patient with a carrier.

5. The method according to claim 1, wherein the patient is a mammal.

6. The method according to claim 1, wherein the patient is human.

7. The method according to claim 1, wherein said administration is parenteral administration.

8. The method according to claim 1, wherein said administration is intratumoral administration.

* * * * *

SEQUENCE LISTING

<160> NUMBER OF SEQ ID NOS: 11

<210> SEQ ID NO 1

```
<211> LENGTH: 43
<212> TYPE: PRT
<213> ORGANISM: Homo sapiens
<220> FEATURE:
<221> NAME/KEY: PEPTIDE
<222> LOCATION: (1)..(43)
<223> OTHER INFORMATION: A-beta 1-43 peptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 2
<211> LENGTH: 42
<212> TYPE: PRT
<213> ORGANISM: Homo sapiens
<220> FEATURE:
<221> NAME/KEY: PEPTIDE
<222> LOCATION: (1)..(42)
<223> OTHER INFORMATION: A-beta 1-42 peptide

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: A-beta 1-40 peptide

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 4
<211> LENGTH: 40
<212> TYPE: PRT
<213> ORGANISM: Artificial Sequence
<220> FEATURE:
<223> OTHER INFORMATION: scrambled A-beta 1-40 peptide

<400> SEQUENCE: 4

Val Ile Gly Lys Tyr His Gly Met Ser Asn Leu Val Gly Arg Ser Phe
1               5                   10                  15

Glu Val His Gln Gly Lys Gly Ala Glu Val Asp Ala His Gly Leu Phe
            20                  25                  30

Asp Ile Glu Ala Phe Val Asp Val
        35                  40
```

<210> SEQ ID NO 5
<211> LENGTH: 770
<212> TYPE: PRT
<213> ORGANISM: Homo sapiens
<220> FEATURE:
<221> NAME/KEY: MISC_FEATURE
<222> LOCATION: (1)..(770)
<223> OTHER INFORMATION: Amyloid precursor protein

<400> SEQUENCE: 5

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

```
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
        370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
                420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
        450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
                500                 505                 510
Glu His Val Arg Met Val Asp Pro Lys Lys Ala Ala Gln Ile Arg Ser
        515                 520                 525
Gln Val Met Thr His Leu Arg Val Ile Tyr Glu Arg Met Asn Gln Ser
        530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
                580                 585                 590
Leu Met Pro Ser Leu Thr Glu Thr Lys Thr Thr Val Glu Leu Leu Pro
        595                 600                 605
Val Asn Gly Glu Phe Ser Leu Asp Asp Leu Gln Pro Trp His Ser Phe
        610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
                660                 665                 670
Ala Glu Phe Arg His Asp Ser Gly Tyr Glu Val His His Gln Lys Leu
        675                 680                 685
Val Phe Phe Ala Glu Asp Val Gly Ser Asn Lys Gly Ala Ile Ile Gly
        690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
                740                 745                 750
Gln Gln Asn Gly Tyr Glu Asn Pro Thr Tyr Lys Phe Phe Glu Gln Met
        755                 760                 765

Gln Asn
```

770

<210> SEQ ID NO 6
<211> LENGTH: 3579
<212> TYPE: DNA
<213> ORGANISM: Homo sapiens
<220> FEATURE:
<221> NAME/KEY: misc_feature
<222> LOCATION: (1)..(3579)
<223> OTHER INFORMATION: nucleotide encoding Amyloid precursor protein

<400> SEQUENCE: 6

| | | | | | |
|---|---|---|---|---|---|
| agtttcctcg | gcagcggtag | gcgagagcac | gcggaggagc | gtgcgcgggg | gccccgggag | 60 |
| acggcggcgg | tggcggcgcg | ggcagagcaa | ggacgcggcg | gatcccactc | gcacagcagc | 120 |
| gcactcggtg | ccccgcgcag | ggtcgcgatg | ctgcccggtt | tggcactgct | cctgctggcc | 180 |
| gcctggacgg | ctcgggcgct | ggaggtaccc | actgatggta | atgctggcct | gctggctgaa | 240 |
| ccccagattg | ccatgttctg | tggcagactg | aacatgcaca | tgaatgtcca | gaatgggaag | 300 |
| tgggattcag | atccatcagg | gaccaaaacc | tgcattgata | ccaaggaagg | catcctgcag | 360 |
| tattgccaag | aagtctaccc | tgaactgcag | atcaccaatg | tggtagaagc | caaccaacca | 420 |
| gtgaccatcc | agaactggtg | caagcggggc | cgcaagcagt | gcaagaccca | tccccacttt | 480 |
| gtgattccct | accgctgctt | agttggtgag | tttgtaagtg | atgcccttct | cgttcctgac | 540 |
| aagtgcaaat | tcttacacca | ggagaggatg | gatgtttgcg | aaactcatct | tcactggcac | 600 |
| accgtcgcca | agagacatgc | agtgagaag | agtaccaact | tgcatgacta | cggcatgttg | 660 |
| ctgccctgcg | gaattgacaa | gttccgaggg | gtagagtttg | tgtgttgccc | actggctgaa | 720 |
| gaaagtgaca | atgtggattc | tgctgatgcg | gaggaggatg | actcggatgt | ctggtggggc | 780 |
| ggagcagaca | cagactatgc | agatgggagt | gaagacaaag | tagtagaagt | agcagaggag | 840 |
| gaagaagtgg | ctgaggtgga | agaagaagaa | gccgatgatg | acgaggacga | tgaggatggt | 900 |
| gatgaggtag | aggaagaggc | tgaggaaccc | tacgaagaag | ccacagagag | aaccaccagc | 960 |
| attgccacca | ccaccaccac | caccacagag | tctgtggaag | aggtggttcg | agaggtgtgc | 1020 |
| tctgaacaag | ccgagacggg | gccgtgccga | gcaatgatct | cccgctggta | ctttgatgtg | 1080 |
| actgaaggga | agtgtgcccc | attctttac | ggcggatgtg | gcggcaaccg | gaacaacttt | 1140 |
| gacacagaag | agtactgcat | ggccgtgtgt | ggcagcgcca | tgtcccaaag | tttactcaag | 1200 |
| actacccagg | aacctcttgc | ccagatcct | gttaaacttc | ctacaacagc | agccagtacc | 1260 |
| cctgatgccg | ttgacaagta | tctcgagaca | cctggggatg | agaatgaaca | tgcccatttc | 1320 |
| cagaaagcca | agagaggct | tgaggccaag | caccgagaga | gaatgtccca | ggtcatgaga | 1380 |
| gaatgggaag | aggcagaacg | tcaagcaaag | aacttgccta | aagctgataa | gaaggcagtt | 1440 |
| atccagcatt | tccaggagaa | agtggaatct | ttggaacagg | aagcagccaa | cgagagacag | 1500 |
| cagctggtgg | agacacacat | ggccagagtg | gaagccatgc | tcaatgaccg | ccgccgcctg | 1560 |
| gccctggaga | actacatcac | cgctctgcag | gctgttcctc | ctcggcctcg | tcacgtgttc | 1620 |
| aatatgctaa | agaagtatgt | ccgcgcagaa | cagaaggaca | gacagcacac | cctaaagcat | 1680 |
| ttcgagcatg | tgcgcatggt | ggatcccaag | aaagccgctc | agatccggtc | ccaggttatg | 1740 |
| acacacctcc | gtgtgattta | tgagcgcatg | aatcagtctc | tctccctgct | ctacaacgtg | 1800 |
| cctgcagtgg | ccgaggagat | tcaggatgaa | gttgatgagc | tgcttcagaa | agagcaaaac | 1860 |
| tattcagatg | acgtcttggc | caacatgatt | agtgaaccaa | ggatcagtta | cggaaacgat | 1920 |
| gctctcatgc | catctttgac | cgaaacgaaa | accaccgtgg | agctccttcc | cgtgaatgga | 1980 |

-continued

```
gagttcagcc tggacgatct ccagccgtgg cattcttttg gggctgactc tgtgccagcc    2040
aacacagaaa acgaagttga gcctgttgat gcccgccctg ctgccgaccg aggactgacc    2100
actcgaccag gttctgggtt gacaaatatc aagacggagg agatctctga agtgaagatg    2160
gatgcagaat tccgacatga ctcaggatat gaagttcatc atcaaaaatt ggtgttcttt    2220
gcagaagatg tgggttcaaa caaggtgca atcattggac tcatggtggg cggtgttgtc    2280
atagcgacag tgatcgtcat caccttggtg atgctgaaga agaaacagta cacatccatt    2340
catcatggtg tggtggaggt tgacgccgct gtcaccccag aggagcgcca cctgtccaag    2400
atgcagcaga acggctacga aaatccaacc tacaagttct tgagcagat gcagaactag    2460 accccccgcca cagcagcctc tgaagttgga cagcaaaacc attgcttcac tacccatcgg    2520
tgtccattta tagaataatg tgggaagaaa caaacccgtt ttatgattta ctcattatcg    2580
ccttttgaca gctgtgctgt aacacaagta gatgcctgaa cttgaattaa tccacacatc    2640
agtaatgtat tctatctctc tttacatttt ggtctctata ctacattatt aatgggtttt    2700
gtgtactgta aagaatttag ctgtatcaaa ctagtgcatg aatagattct ctcctgatta    2760
tttatcacat agccccttag ccagttgtat attattcttg tggtttgtga cccaattaag    2820
tcctacttta catatgcttt aagaatcgat ggggatgct tcatgtgaac gtgggagttc    2880
agctgcttct cttgcctaag tattcctttc ctgatcacta tgcattttaa agttaaacat    2940
ttttaagtat ttcagatgct ttagagagat tttttttcca tgactgcatt ttactgtaca    3000
gattgctgct tctgctatat ttgtgatata ggaattaaga ggatacacac gtttgtttct    3060
tcgtgcctgt tttatgtgca cacattaggc attgagactt caagcttttc tttttttgtc    3120
cacgtatctt tgggtctttg ataaagaaaa gaatccctgt tcattgtaag cacttttacg    3180
gggcgggtgg ggaggggtgc tctgctggtc ttcaattacc aagaattctc caaaacaatt    3240
ttctgcagga tgattgtaca gaatcattgc ttatgacatg atcgctttct acactgtatt    3300
acataaataa attaaataaa ataaccccgg gcaagacttt tctttgaagg atgactacag    3360
acattaaata atcgaagtaa ttttgggtgg ggagaagagg cagattcaat tttctttaac    3420
cagtctgaag tttcatttat gatacaaaag aagatgaaaa tggaagtggc aatataaggg    3480
gatgaggaag gcatgcctgg acaaacccctt cttttaagat gtgtcttcaa tttgtataaa    3540
atggtgtttt catgtaaata aatacattct tggaggagc                            3579
```

<210> SEQ ID NO 7
<211> LENGTH: 42
<212> TYPE: PRT
<213> ORGANISM: Artificial Sequence
<220> FEATURE:
<223> OTHER INFORMATION: 21G-A-beta 1-42 (Flemish) mutant

<400> SEQUENCE: 7

Asp Ala Glu Phe Arg His Asp Ser Gly Tyr Glu Val His His Gln Lys
1               5                   10                  15

Leu Val Phe Phe Gly Glu Asp Val Gly Ser Asn Lys Gly Ala Ile Ile
            20                  25                  30

Gly Leu Met Val Gly Gly Val Val Ile Ala
        35                  40

<210> SEQ ID NO 8
<211> LENGTH: 42
<212> TYPE: PRT
<213> ORGANISM: Artificial Sequence

```
<220> FEATURE:
<223> OTHER INFORMATION: 22Q-A-beta 1-42 (Dutch) mutant

<400> SEQUENCE: 8

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala Ile Ile
            20                  25                  30

Gly Leu Met Val Gly Gly Val Val Ile Ala
        35                  40

<210> SEQ ID NO 9
<211> LENGTH: 42
<212> TYPE: PRT
<213> ORGANISM: Artificial Sequence
<220> FEATURE:
<223> OTHER INFORMATION: 22K-A-beta 1-42 (Italian) mutant

<400> SEQUENCE: 9

Asp Ala Glu Phe Arg His Asp Ser Gly Tyr Glu Val His His Gln Lys
1               5                   10                  15

Leu Val Phe Phe Ala Lys Asp Val Gly Ser Asn Lys Gly Ala Ile Ile
            20                  25                  30

Gly Leu Met Val Gly Gly Val Val Ile Ala
        35                  40

<210> SEQ ID NO 10
<211> LENGTH: 42
<212> TYPE: PRT
<213> ORGANISM: Artificial Sequence
<220> FEATURE:
<223> OTHER INFORMATION: 22G-A-beta 1-42 (Arctic) mutant

<400> SEQUENCE: 10

Asp Ala Glu Phe Arg His Asp Ser Gly Tyr Glu Val His His Gln Lys
1               5                   10                  15

Leu Val Phe Phe Ala Gly Asp Val Gly Ser Asn Lys Gly Ala Ile Ile
            20                  25                  30

Gly Leu Met Val Gly Gly Val Val Ile Ala
        35                  40

<210> SEQ ID NO 11
<211> LENGTH: 42
<212> TYPE: PRT
<213> ORGANISM: Artificial Sequence
<220> FEATURE:
<223> OTHER INFORMATION: 23N-A-beta 1-42 (Iowa) mutant

<400> SEQUENCE: 11

Asp Ala Glu Phe Arg His Asp Ser Gly Tyr Glu Val His His Gln Lys
1               5                   10                  15

Leu Val Phe Phe Ala Glu Asn Val Gly Ser Asn Lys Gly Ala Ile Ile
            20                  25                  30

Gly Leu Met Val Gly Gly Val Val Ile Ala
        35                  40
```